United States Patent
Tennican

(10) Patent No.: US 9,592,375 B2
(45) Date of Patent: Mar. 14, 2017

(54) INTRAVASCULAR LINE AND PORT CLEANING METHODS, METHODS OF ADMINISTERING AN AGENT INTRAVASCULARLY, METHODS OF OBTAINING/TESTING BLOOD, AND DEVICES FOR PERFORMING SUCH METHODS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

(*) Notice: Subject to any disclaimer, the term of this patent is extended or adjusted under 35 U.S.C. 154(b) by 0 days.

(21) Appl. No.: 13/781,196

(22) Filed: Feb. 28, 2013

(65) Prior Publication Data

US 2013/0178804 A1 Jul. 11, 2013

Related U.S. Application Data

(63) Continuation-in-part of application No. 13/571,757, filed on Aug. 10, 2012, which is a continuation of
(Continued)

(51) Int. Cl.
*A61M 39/18* (2006.01)
*A61M 39/16* (2006.01)
(Continued)

(52) U.S. Cl.
CPC ............. *A61M 39/18* (2013.01); *A61B 90/70* (2016.02); *A61M 39/162* (2013.01);
(Continued)

(58) Field of Classification Search
CPC ............................. A61M 39/162; A61B 19/34
(Continued)

(56) References Cited

U.S. PATENT DOCUMENTS

| 470,461 A | 3/1892 | Banta et al. |
| D102,368 S | 12/1936 | Higgins |

(Continued)

FOREIGN PATENT DOCUMENTS

| CN | 1035439 | 9/1989 |
| CN | 1178476 | 4/1998 |

(Continued)

OTHER PUBLICATIONS

Menyhay, Steve Z., "Disinfection of Needleless Catheter Connectors and Access Ports with Alcohol May Not Prevent Microbial Entry: The Promise of a Novel Antiseptic-Barrier Cap", Infection Control and Hospital Epidemiology, Jan. 2006, vol. 27, No. 1, pp. 23-27.

(Continued)

*Primary Examiner* — Laura Bouchelle
*Assistant Examiner* — Anh Bui
(74) *Attorney, Agent, or Firm* — Wells St. John P.S.

(57) ABSTRACT

A syringe assembly is provided comprising a syringe cylinder extending from an opening configured to receive a plunger to an end configured to couple with a needle and/or medical tubing, a cap configured to couple to the end, and barrier material at least partially encompassing the cap and the end. A syringe assembly is provided comprising a syringe cylinder extending from an opening configured to receive a plunger to an end configured to couple with a needle and/or medical tubing, a plunger extending from one end to a seal end, and at least one cap configured to couple to the one end. A syringe assembly is provided comprising a syringe cylinder extending from an opening configured to receive a plunger to an end configured to couple with a needle and/or medical tubing, and a plunger extending from one end to a seal end, the one end of the plunger defining a recess configured to receive at least one cap.

8 Claims, 28 Drawing Sheets

Related U.S. Application Data application No. 13/184,371, filed on Jul. 15, 2011, now Pat. No. 8,262,643, which is a continuation of application No. 11/745,843, filed on May 8, 2007, now Pat. No. 8,162,899.

(60) Provisional application No. 61/605,095, filed on Feb. 29, 2012, provisional application No. 60/747,606, filed on May 18, 2006, provisional application No. 60/842,194, filed on Aug. 31, 2006, provisional application No. 60/895,621, filed on Mar. 19, 2007.

(51) Int. Cl.
*A61M 39/20* (2006.01)
*A61M 5/00* (2006.01)

(52) U.S. Cl.
CPC .......... *A61M 39/165* (2013.01); *A61M 39/20* (2013.01); *A61M 5/002* (2013.01); *A61M 2209/06* (2013.01)

(58) Field of Classification Search
USPC .................................................. 604/905, 192
See application file for complete search history.

(56) References Cited

U.S. PATENT DOCUMENTS

| | | | |
|---|---|---|---|
| 2,851,036 A * | 9/1958 | Lipari | 600/578 |
| 2,961,682 A | 11/1960 | Wurmbock et al. | |
| 3,270,743 A | 9/1966 | Gingras | |
| 3,342,180 A * | 9/1967 | Sandhage | A61M 5/284 604/192 |
| D212,871 S | 12/1968 | Anderson | |
| 3,822,702 A | 7/1974 | Bolduc | |
| 3,871,374 A | 3/1975 | Bolduc et al. | |
| 3,875,939 A | 4/1975 | Bolduc et al. | |
| 3,887,112 A | 6/1975 | Bolduc et al. | |
| 3,948,259 A | 4/1976 | Bolduc et al. | |
| 3,972,331 A | 8/1976 | Bolduc et al. | |
| 4,041,934 A | 8/1977 | Genese | |
| 4,126,134 A | 11/1978 | Bolduc et al. | |
| 4,417,890 A | 11/1983 | Dennehey et al. | |
| 4,424,057 A | 1/1984 | House | |
| 4,432,764 A | 2/1984 | Lopez | |
| 4,440,207 A | 4/1984 | Genatempo et al. | |
| 4,444,310 A | 4/1984 | Odell | |
| 4,461,368 A | 7/1984 | Plourde | |
| 4,482,348 A * | 11/1984 | Dent | 604/198 |
| 4,624,664 A | 11/1986 | Peluso et al. | |
| 4,703,762 A | 11/1987 | Rathbone et al. | |
| 4,728,321 A | 3/1988 | Chen | |
| 4,778,447 A | 10/1988 | Velde | |
| 4,781,704 A | 11/1988 | Potter | |
| 4,799,926 A * | 1/1989 | Haber | 604/187 |
| 4,811,847 A | 3/1989 | Reif et al. | |
| 4,893,956 A | 1/1990 | Wojcik et al. | |
| 4,929,232 A | 5/1990 | Sweeney | |
| 4,983,161 A | 1/1991 | Dadson | |
| 5,100,621 A | 3/1992 | Berke et al. | |
| 5,125,415 A | 6/1992 | Bell | |
| 5,135,514 A | 8/1992 | Kimber | |
| 5,224,936 A | 7/1993 | Gallagher | |
| 5,242,425 A | 9/1993 | White et al. | |
| 5,379,888 A | 1/1995 | Rentos | |
| 5,471,706 A | 12/1995 | Wallock et al. | |
| 5,554,135 A | 9/1996 | Menyhay | |
| 5,580,530 A | 12/1996 | Kowatsch et al. | |
| 5,641,464 A | 6/1997 | Briggs, III et al. | |
| 5,670,193 A | 9/1997 | Vreugde | |
| 5,694,978 A | 12/1997 | Heilmann et al. | |
| 5,722,537 A | 3/1998 | Sigler | |
| 5,792,120 A | 8/1998 | Menyhay | |
| 5,813,992 A | 9/1998 | Henwood | |
| 5,851,200 A | 12/1998 | Higashikawa et al. | |
| 5,989,229 A | 11/1999 | Chiappetta | |
| 6,045,539 A | 4/2000 | Menyhay | |
| 6,083,002 A | 7/2000 | Martin et al. | |
| 6,196,998 B1 | 3/2001 | Jansen et al. | |
| 6,206,134 B1 | 3/2001 | Stark et al. | |
| 6,210,064 B1 | 4/2001 | White et al. | |
| 6,827,766 B2 | 12/2004 | Carnes et al. | |
| 7,011,650 B2 | 3/2006 | Rosoff et al. | |
| 7,083,605 B2 | 8/2006 | Miyahara | |
| 7,198,611 B2 | 4/2007 | Connell et al. | |
| 7,282,186 B2 | 10/2007 | Lake, Jr. et al. | |
| 7,322,941 B2 | 1/2008 | Henshaw | |
| 7,452,349 B2 | 11/2008 | Miyahara | |
| 7,780,794 B2 | 8/2010 | Rogers et al. | |
| 8,740,864 B2 | 6/2014 | Hoang et al. | |
| 2003/0146246 A1 | 8/2003 | Arsenault et al. | |
| 2003/0153865 A1 | 8/2003 | Connell et al. | |
| 2004/0182735 A1 | 9/2004 | Lombardi et al. | |
| 2004/0258560 A1 | 12/2004 | Lake et al. | |
| 2005/0029286 A1 | 2/2005 | Bergin et al. | |
| 2005/0051572 A1 | 3/2005 | Vogel et al. | |
| 2005/0124946 A1 | 6/2005 | Landau et al. | |
| 2005/0214185 A1 | 9/2005 | Castaneda | |
| 2006/0030827 A1 | 2/2006 | Raulerson et al. | |
| 2006/0106349 A1 | 5/2006 | Kito et al. | |
| 2007/0112333 A1 * | 5/2007 | Hoang | A61M 39/02 604/533 |
| 2007/0244368 A1 | 10/2007 | Bayloff et al. | |
| 2007/0282280 A1 | 12/2007 | Tennican | |
| 2008/0019889 A1 | 1/2008 | Rogers et al. | |
| 2008/0021414 A1 | 1/2008 | Alheidt | |
| 2008/0086091 A1 | 4/2008 | Anderson et al. | |
| 2008/0095680 A1 | 4/2008 | Steffens et al. | |
| 2008/0147047 A1 | 6/2008 | Davis et al. | |
| 2008/0154200 A1 | 6/2008 | Lesch | |
| 2009/0099529 A1 * | 4/2009 | Anderson | A61M 5/31511 604/192 |
| 2011/0290799 A1 | 12/2011 | Anderson et al. | |
| 2012/0216359 A1 | 8/2012 | Rogers et al. | |
| 2012/0283693 A1 | 11/2012 | Anderson et al. | |
| 2012/0296284 A1 | 11/2012 | Anderson et al. | |
| 2012/0302970 A1 | 11/2012 | Tennican | |
| 2013/0023828 A1 | 1/2013 | Anderson et al. | |
| 2013/0035667 A1 | 2/2013 | Anderson et al. | |
| 2015/0018774 A1 | 1/2015 | Anderson et al. | |

FOREIGN PATENT DOCUMENTS

| | | |
|---|---|---|
| CN | 1258471 | 7/2000 |
| CN | 2013800225723 | 12/2015 |
| CN | 201380022572 | 10/2016 |
| EP | 0815884 | 1/1998 |
| EP | 1563863 | 8/2005 |
| EP | 07797491 | 12/2010 |
| EP | 07797491 | 12/2013 |
| EP | 13755538 | 9/2015 |
| FR | 2782910 | 3/2000 |
| GB | 1470571 | 4/1977 |
| JP | 50-026394 | 3/1975 |
| JP | 63-500639 | 3/1988 |
| JP | H06-254161 | 9/1994 |
| JP | 2002-536090 | 10/2002 |
| JP | 2005-312932 | 11/2005 |
| JP | 2007-061476 | 3/2007 |
| TW | 200404153 | 3/2004 |
| TW | 096117826 | 8/2013 |
| WO | WO 87/00441 | 1/1987 |
| WO | WO 9628201 | 9/1996 |
| WO | WO 98/36789 | 8/1998 |
| WO | WO 98/53868 | 12/1998 |
| WO | WO 00/46126 | 8/2000 |
| WO | WO 2005/070484 | 8/2005 |
| WO | WO 2006/019782 | 2/2006 |
| WO | WO PCT/US07/69015 | 9/2008 |
| WO | WO2009/002474 | 12/2008 |
| WO | WO PCT/US07/69015 | 9/2009 |

(56) References Cited

FOREIGN PATENT DOCUMENTS

| WO | WO 2011/053924 | 5/2011 |
| WO | WO PCT/US2013/028437 | 6/2013 |
| WO | WO PCT/US13/028437 | 9/2014 |

OTHER PUBLICATIONS

Office Action for U.S. Appl. No. 13/572,325, Mailed on Jun. 4, 2015, Patrick O. Tennican, "Medical Caps and Medical Cap for Manufacturing Methods," 12 pages.
Office Action for U.S. Appl. No. 13/572,325, Mailed on Dec. 17, 2014, Tennican, "Medical Caps and Methods of Use", 15 pages.
"DuPont Hytrel Product Information," DuPont: The Miracles of Science (copyright 2001).

* cited by examiner

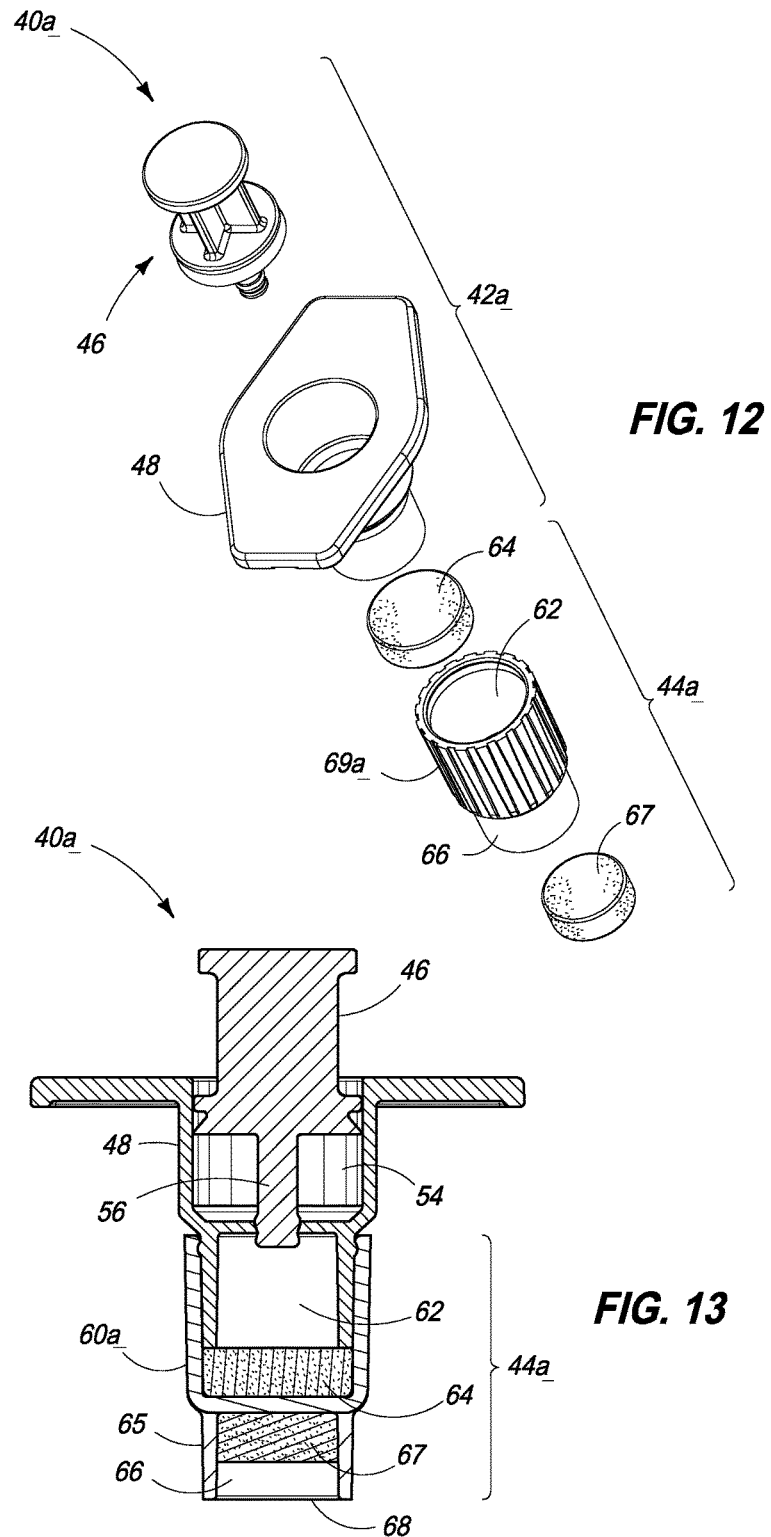

INTRAVASCULAR LINE AND PORT CLEANING METHODS, METHODS OF ADMINISTERING AN AGENT INTRAVASCULARLY, METHODS OF OBTAINING/TESTING BLOOD, AND DEVICES FOR PERFORMING SUCH METHODS

CROSS REFERENCE TO RELATED APPLICATION

This application claims priority to U.S. Provisional Patent Application Ser. No. 61/605,095 which was filed on Feb. 29, 2012, and is a continuation-in-part of U.S. patent application Ser. No. 13/571,757 which was filed Aug. 10, 2012, which is a continuation of U.S. patent application Ser. No. 13/184,371 filed Jul. 15, 2011, which is a continuation of U.S. patent application Ser. No. 11/745,843 filed May 8, 2007, now U.S. Pat. No. 8,162,899 which claims priority under 35 U.S.C. §119 to U.S. Provisional Application No. 60/747,606, which was filed May 18, 2006; and to U.S. Provisional Application No. 60/842,194, which was filed Aug. 31, 2006, and claims priority to U.S. Provisional Application No. 60/895,621, which was filed Mar. 19, 2007, the entirety of each of which is incorporated by reference herein.

TECHNICAL FIELD

The disclosure pertains to intravascular port access devices, intravascular port cleaning devices, methods of cleaning an intravascular port, methods of administering an agent into an intravascular line port, methods of obtaining a blood sample from an individual, and sets of intravascular line port caps.

BACKGROUND

Intravenous lines, such as peripheral IV lines and central IV lines, are common intravenous access methods for administering medicants, nutrient solutions, blood products, or other substances into a vein. Arterial lines are used, for example, in monitoring physiological parameters by arterial blood sampling during coronary, intensive or critical care. However, microorganism intravascular device colonization or infection can occur as a result from a patients' own endogenous flora or from microorganisms introduced from contaminated equipment or other environmental contamination sources. As a result, localized or systemic infection or septicemia can occur and can be life threatening.

Introduction of microorganisms into an intravenous line can be initiated or facilitated during handling of a catheter, hub, associated tubing, equipment, or injection ports, especially during manipulation of lines in preparation and during initiation of fluid administration into or withdrawal from the line. Microorganisms present on a surface of an injection port can be introduced through the port during administration. Microorganisms present on contaminated equipment utilized for administration can be introduced through the port causing colonization or infection. Bacterial growth and/or aggregation in a port or catheter can serve as the nidus for clotting, embolization and/or occlusion of the port or catheter. Further manipulation or administration through the port can facilitate spreading of microorganisms within the port, catheter, and lines, and ultimately into the patient's vein/artery and/or surrounding tissue. Accordingly, it would be advantageous to develop methods and devices for cleaning of external surfaces of intravascular access ports and/or internal port areas to reduce risks of colonization and infection.

Another complication that can occur in association with an intravascular line, catheter or access port is clot formation due to blood return. Initial clot formation could extend and/or embolizento the superior vena cava and/or the right atrium and/or right ventricle of the heart, and subsequently into the pulmonary system circulating to the lungs. It would be advantageous to develop methodology and devices to deliver clot dissolving or clot inhibitory agents through intravascular ports to minimize or eliminate intravascular port associated clotting.

Yet another issue that can be associated with intravascular lines is lipid accumulation or build-up within the line or port. It would be advantageous to develop methodology and devices to deliver lipolytic agents through intravascular ports to minimize or eliminate port associated lipid build up.

SUMMARY OF THE DISCLOSURE

In one aspect the disclosure pertains to an intravascular port access device. The device includes a first component having a chamber and being configured to attach reversibly to an intravenous line port. The second component reversibly attaches to the first component and contains a disinfecting agent and an applicator material selected from the group consisting of polyethylene felt sponge, polyethylene foam sponge, plastic foam sponge and silicon foam sponge and other sponge-like or absorbant materials. The second component is configured to be reversibly received over external surfaces of the intravenous line port.

In one aspect the disclosure encompasses an intravascular line port cleaner including a syringe barrel having a first end and a second end. A slideable piston is received into the barrel through the second end. The line port cleaner includes a first cap containing a cleansing agent and a second cap containing a microbiocidal agent.

In one aspect the disclosure encompasses a method of cleansing an intravenous line port. The method includes providing a port cleaning device comprising a first component having a chamber with a first cleaning agent. A second component includes a second cleaning agent. A third component has a microbiocidal agent and is reversibly attached to the first component. The method includes removing a second component from the device, contacting the external surfaces of the port with the second cleaning agent, injecting the first cleaning agent from the chamber into the port, removing the third component from the device, and capping the port with the third component.

In one aspect the disclosure encompasses a method of obtaining a blood sample from an individual. The method includes providing a port access device having a first component including a chamber, a second component containing a cleaning agent and a third component comprising a microbiocidal agent. The third component is reversibly attached to the first component. The method includes removing the second component from the device and contacting the external surfaces of the port with the cleaning agent. The method further includes drawing blood from the individual through the port into the chamber of the first component removing the third component from the device and capping the port with the third component.

In one aspect the disclosure includes a set of intravascular line port caps. The set of caps includes a first port cap containing a first agent and a first applicator material. The set further includes a second port cap containing a second agent and a second applicator material.

The disclosure also provides syringe assemblies that can include: a syringe cylinder extending from an opening configured to receive a plunger to an end configured to couple with a needle and/or medical tubing; a cap configured to couple to the end; and barrier material at least partially encompassing the cap and the end. Syringe assemblies can also include: a syringe cylinder extending from an opening configured to receive a plunger to an end configured to couple with a needle and/or medical tubing; a plunger extending from one end to a seal end; and at least one cap configured to couple to the one end. Additional syringe assemblies can include: a syringe cylinder extending from an opening configured to receive a plunger to an end configured to couple with a needle and/or medical tubing; and a plunger extending from one end to a seal end, the one end of the plunger defining a recess configured to receive at least one cap.

DRAWINGS

Embodiments of the disclosure are described below with reference to the following accompanying drawings.

FIG. 12 is a diagrammatic exploded view of a device in accordance with another aspect of the disclosure.

FIG. 13 is a diagrammatic cross-sectional view of the device shown in FIG. 12.

DESCRIPTION

This disclosure of the disclosure is submitted in furtherance of the constitutional purposes of the U.S. Patent Laws "to promote the progress of science and useful arts" (Article 1, Section 8).

In general the disclosure includes devices and methodology for cleaning and/or accessing intravascular line ports. In particular applications devices of the disclosure can be used for cleaning external surfaces of a intravascular line port followed by cleaning of the port itself and in particular instances cleaning of intravascular lines.

In other applications devices of the disclosure can be utilized for administering an agent intravascularly. During these applications, the devices in accordance with the disclosure can typically be utilized to cleanse external surfaces of the port prior to utilizing the device for administering of an agent intravascularly. In another application devices of the disclosure can be utilized during the process of obtaining a blood sample from an individual. A device in accordance with the disclosure is typically utilized to cleanse external surfaces of a port prior to utilizing the device to withdraw a sample of blood from the port. The disclosure also includes methodology for such port cleansing agent administration and blood sampling techniques.

In one embodiment, the device comprises two components. An example two component device is described with reference to FIGS. 1-5.

Figure 1:
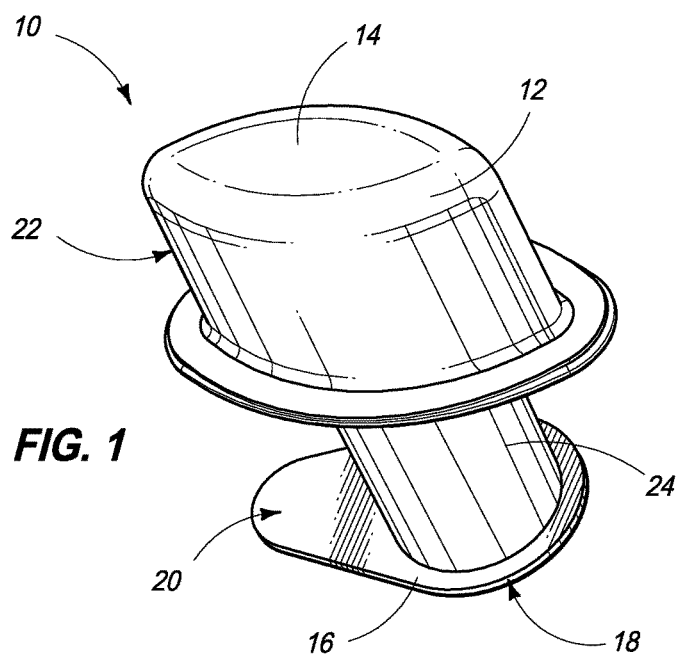
FIG. 1 is a diagrammatic isometric view of a device in accordance with one aspect of the disclosure.
Figure 2:
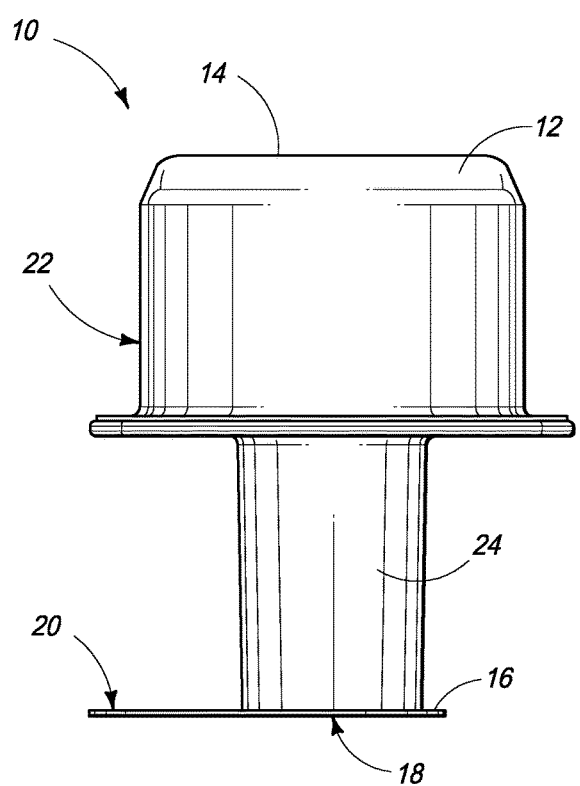
FIG. 2 is a diagrammatic side view of the device shown in FIG. 1.

Referring initially to FIG. 1, a port access device 10 comprises a first component 12 at a first end 14 of the device, and a second component 16 at a second end 18 of the device. Second component 16 can have a tab 20 or other extension feature for assisting removal of the second component from the first component. First component 12 has a chamber housing 22 which can be a collapsible housing. First component 12 can also comprise an extension portion 24. Referring to FIG. 2, as depicted device 10 can have second portion 16 insertable within connector portion 24. It is to be understood however that the disclosure contemplates other configurations wherein second portion 16 fits over or caps extension portion 24. It is also to be understood that the shape and dimension of collapsible housing 22 is but an example with alternative shapes, sizes and configurations contemplated.

Figure 3:
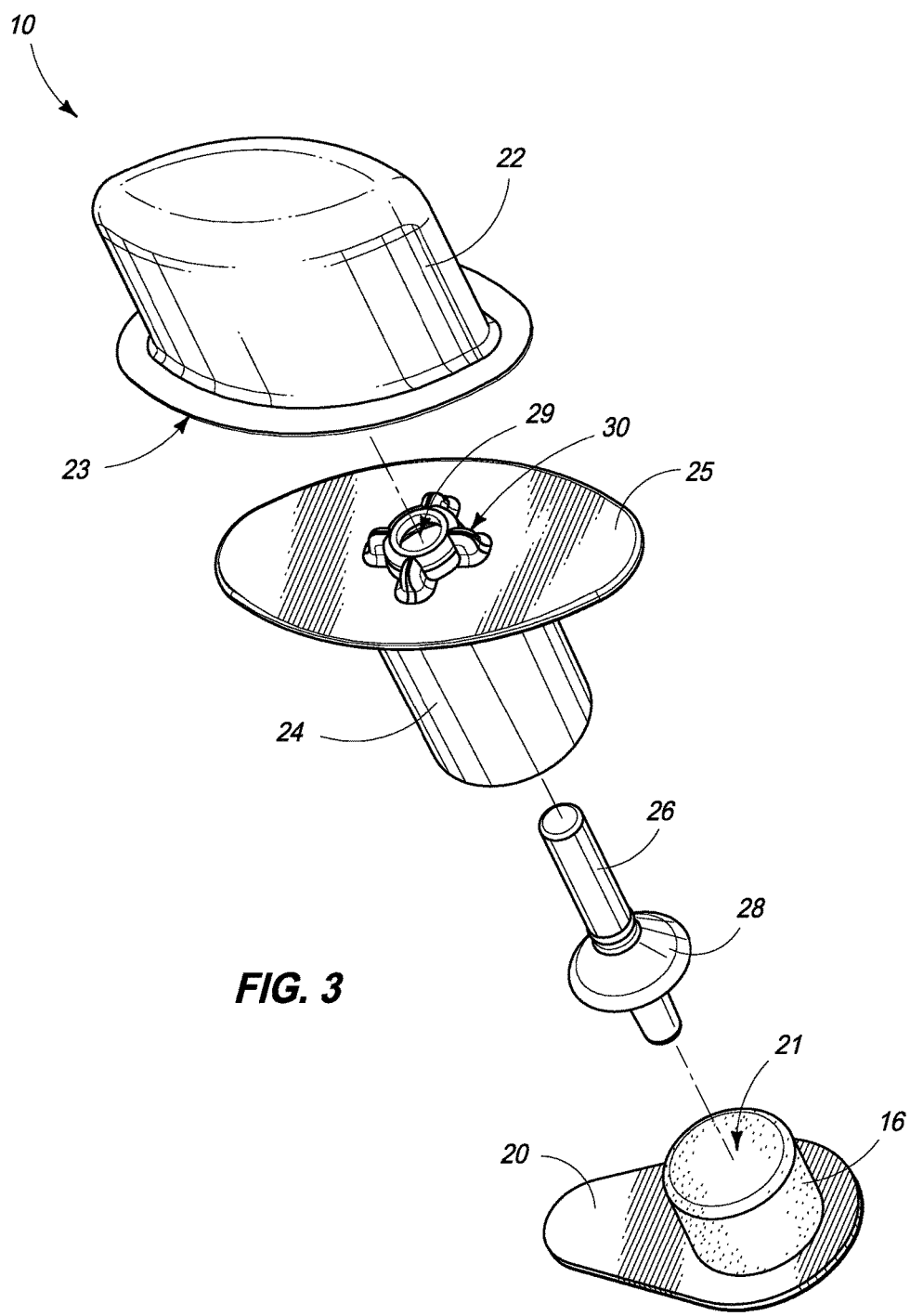
FIG. 3 is a diagrammatic exploded view of the device shown in FIG. 1.

Referring to FIG. 3 such shows an exploded view of the device depicted in FIGS. 1 and 2. As illustrated chamber housing 22 of device 10 can house a chamber 23. Connector 24 can comprise a separator 25 having an opening 29 passing therethrough. Connector 24 can further comprise a receiving port 30 for receiving a dispenser 26. Dispenser 26 in turn can comprise a valve portion 28. Second component 16 can comprise a container 21.

Figure 4:
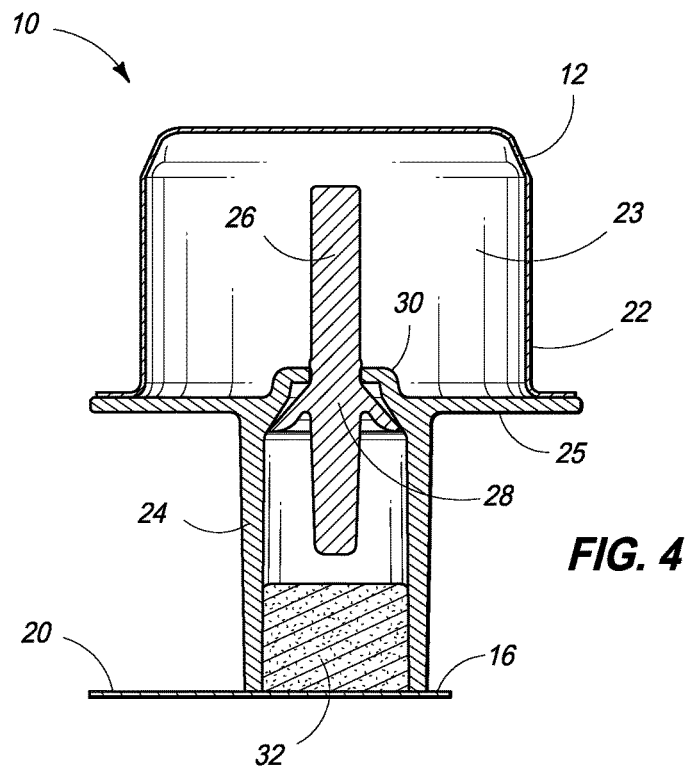
FIG. 4 is a diagrammatic cross-sectional view of the device shown in FIG. 1.
Figure 5:
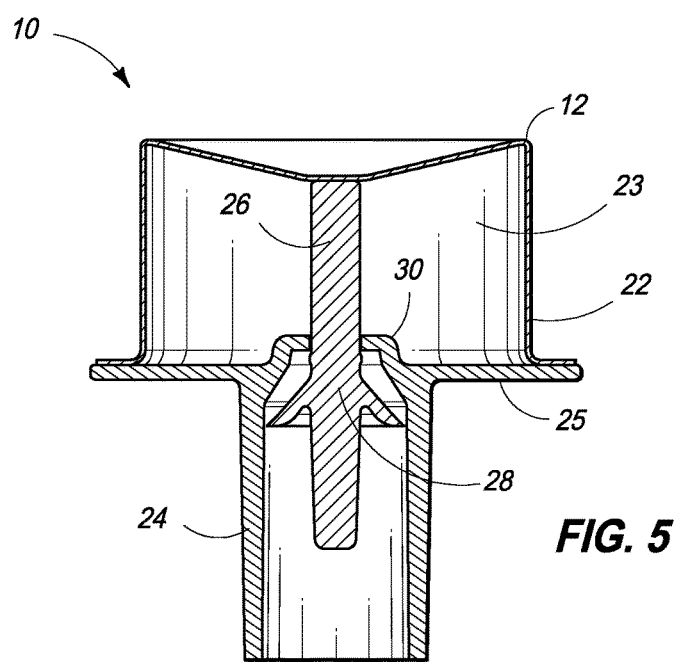
FIG. 5 is a diagrammatic cross-sectional view of the device shown in FIG. 1 after repositioning relative to the positioning depicted in FIG. 4.

Referring next to FIG. 4, such shows dispenser 26 with valve 28 seated within receiving port 30. As depicted such valve mechanism is in the "closed" position where contents of chamber 23 are blocked from passing into or through connector 24. Referring next to FIG. 5, application of force upon collapsible housing 22 such as a downward pressure upon a top surface of the housing can be utilized to displace valve device 28 from receiving port 30 as illustrated. Such displacement can allow passage of the contents of chamber 23 into or through connector portion 24.

As depicted in FIG. 4, second component 16 can contain an applicator material 32. Such applicator material can be for example, a sponge or sponge-type material. Exemplary sponge-type materials can include but are not limited to polyethylene felt sponge, polyethylene foam sponge, plastic foam sponge and silicon foam sponge and other sponge-like materials such as a felt or other absorbant materials.

Where device 10 is to be utilized for port cleansing applications, container 21 of second component 16 will typically contain a cleansing agent. The cleansing agent can be a disinfecting agent for cleansing external port surfaces. The agent is not limited to a particular cleaning or disinfecting agent and can comprise for example alcohol, preferably contained in an alcohol solution comprising from about 5% to about 99% alcohol. In particular applications the alcohol solution will comprise 25% to 90% alcohol. The sponge-type applicator material can be utilized to assist in containing the cleansing agent and can further assist in applying the agent to external surfaces of the intravascular port. Second component 16 is removably attached to the device 10. For cleansing of the port, removable component 16 is removed from first component 12 and is utilized to contact external port surfaces for cleansing of external portions of an intravascular line port.

After cleansing of external portions of the port, the first component of the device, which in cleansing/disinfecting applications can be utilized for internal cleansing of the intravascular port, can be reversibly attached to the port to be cleansed. The chamber volume can be for example up to 3.5 ml; a preferred volume range can be from about 1 to about 3 ml. although alternative chamber sizes for smaller or larger volumes are contemplated. The chamber can have appropriate calibration marks relative to the total volume of the chamber. For example, a 3.5 ml. fluid volume chamber can have volume markings every 1 ml, every 0.5 ml, every 0.1 ml, etc. In particular embodiments, the connector portion can have a LEUR-LOK® (Becton, Dickinson and Company Corp., Franklin Lakes N.J.) fitting (not shown) for connection to a LEUR-LOK® type port. A cleansing agent can be provided within chamber 23 and can be an antibiotic or an alternative appropriate disinfectant. An exemplary agent can be an alcohol or alcohol solution such as described above relative to the second component container 21. In cleansing applications chamber 22 can alternatively or additionally contain chemical agents including ethylene diamine tretaacetic acid (EDTA) and/or sodium citrate, hydrogen peroxide, and other antiseptic or antimicrobial components Once connected to the line port external pressure can be applied to collapsible housing 22 by for example squeezing, pinching, or pushing inward on the housing to displace dispenser 26 thereby opening or displacing valve 28 from receiving port 30. Continued squeezing or external force can be utilized to dispel or eject contents of chamber 23 through connector 24 and into the connected port. Depending upon the volume of chamber 23 the injected cleansing solution may extend into the intravascular line itself. After dispelling the contents of chamber 23 device component 12 can be removed from the port to allow administration of fluids to be delivered intravascularly (for example). If such delivery is not to be performed immediately upon cleansing, component 12 of the cleansing device can be retained on the port until such time as intravascular delivery is desired.

In another aspect, the above-described device and methodology can be utilized for administering an anti-clot agent to minimize or prevent intravascular associated clot formation or to dissolve an existing clot. In this aspect, rather than or in addition to the antimicrobial agent, chamber 23 can contain an appropriate anticoagulant agent or clot dissolving agent. Exemplary anti-clot agents which can be utilized include but are not limited to anticoagulants such as EDTA, sodium citrate, heparin and heparin derivatives, and anti-thrombolytic agents such as tissue plasminogen activator. Where lipid accumulation is an issue an appropriate dispersion or lipolytic agent can be administered, either independently or in combination with antimicrobial agent and/or anti-clot agent. Injection of any such agents can be achieved in a manner analogous to that described above relative to the cleansing agent. These applications may also be accomplished utilizing the embodiments illustrated and described below.

Figure 6:
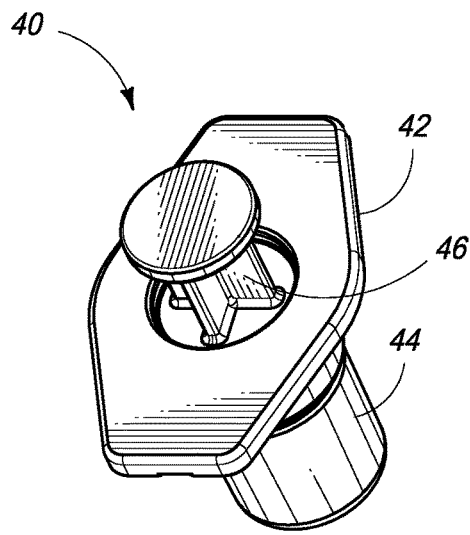
FIG. 6 is a diagrammatic isometric view of a device in accordance with another aspect of the disclosure.
Figure 7:
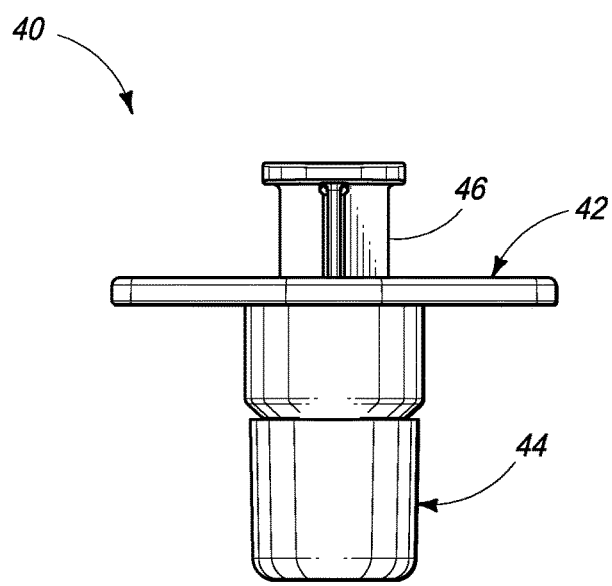
FIG. 7 is a diagrammatic side view of the device shown in FIG. 6.
Figure 8:
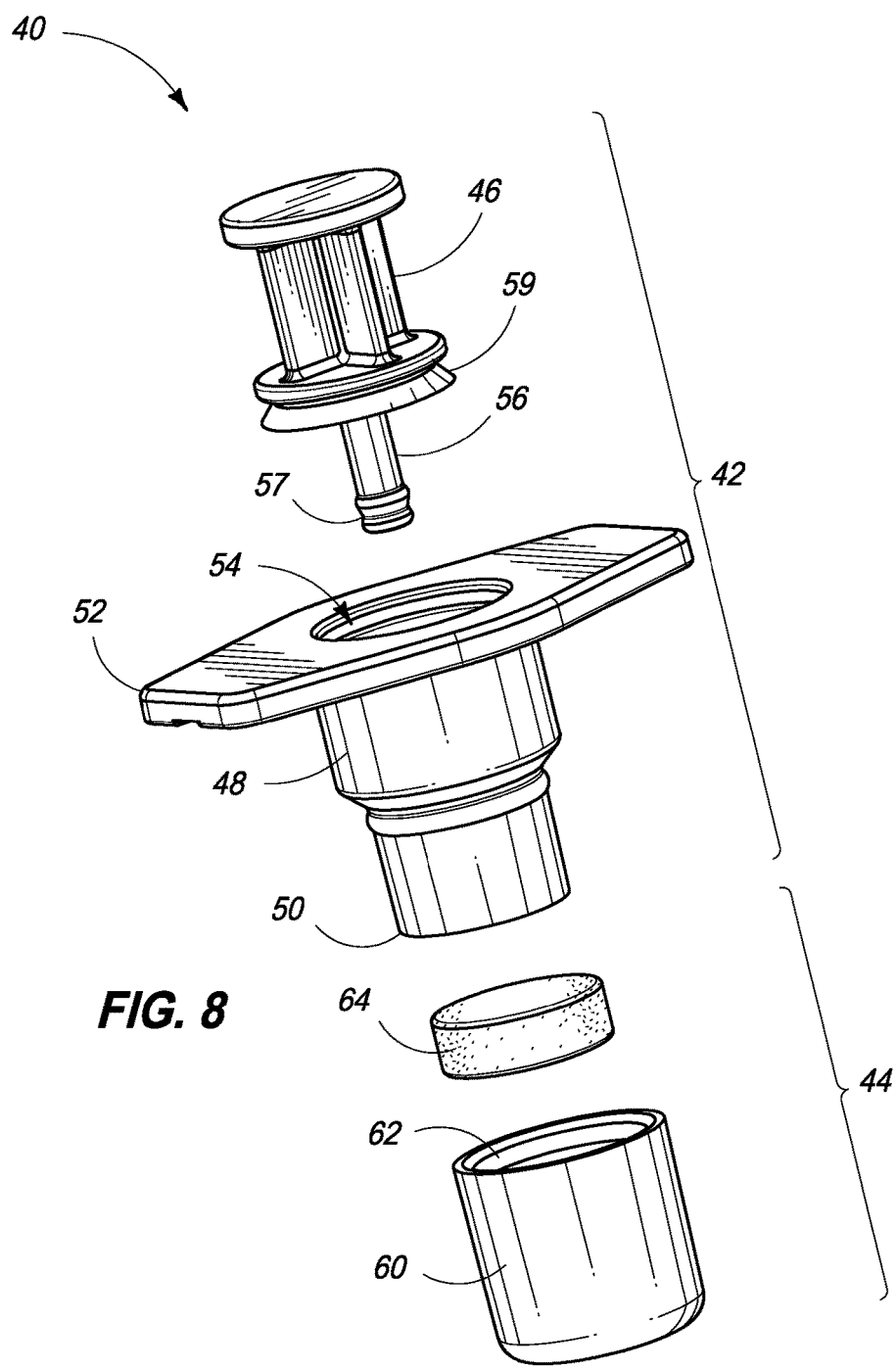
FIG. 8 is a diagrammatic exploded view of the device of FIG. 6.

An alternative embodiment of a device in accordance with the disclosure is illustrated and described with reference to FIGS. 6-11. Referring to FIG. 6, such illustrates an alternative example port access device 40 having a syringe-like first component 42 and a second component 44. Referring to FIG. 7 syringe-like first component 42 includes a plunger 46. An exploded view of the port access device is depicted in FIG. 8. First component 42 includes a syringe barrel-like housing 48 having a first end 50 and a second end 52 with an internal chamber 54. Chamber 54 can preferably have a fluid volume of from 1 to about 3.5 ml. Housing 48 can have appropriate calibration marks as discussed above with respect to the earlier embodiment.

Plunger 46 can include a stem portion 56 having a seal 57. Plunger 46 can be insertable into second end 52 of housing 48. A second seal 59 can be associated with the larger diameter body of the plunger. Seal 59 is preferably present to form a seal between the plunger and an internal surface of the device chamber. Seal 59 can preferably be an elastomeric seal which is over molded onto the piston (which can preferably be a molded hard plastic material). However, the disclosure contemplates alternative seal material and use of non-overmolded techniques.

Seal 57 can be a single seal or a set of seals and can be for example a set of two o-rings, a single broad overmolded elastomeric o-ring or sleeve or a hard plastic seal molded integrally with the piston stem. The presence of seal 57 can advantageously inhibit or prevent unwanted or unintentional backflow of fluid into the device chamber thereby decreasing the risk of contamination of the device and/or its contents. Alternatively relative to the depicted configuration a single seal can be over molded to have base portion which forms the seal between an internal wall of the device chamber and the large diameter portion of the piston and a sleeve portion which covers the walls of the smaller diameter portion of the piston (not shown).

The second component 44 is a removable cap portion having a housing 60 and an internal container 62. Container 62 can contain an applicator material 64. The applicator material can be, for example, any of those materials discussed above with respect to the earlier embodiment. Additionally the applicator material can be shaped in such a way as to facilitate the surface contact between the applicator material and the various concave and/or convex shapes of the implement to be cleaned. The second component 44 can additionally contain a cleansing agent such as those cleansing agents discussed above. Second component 44 preferably can be configured to fit over or onto an intravascular port such that the cleansing agent can be applied to external surfaces of the port. Such cleaning preferably can be conducted prior to administering the contents of chamber 54 (for example, an anti-clot, antimicrobial or other cleansing agent) into the port. However, the disclosure contemplates post-administration cleansing of the port utilizing the removable cap portion.

Figure 9:
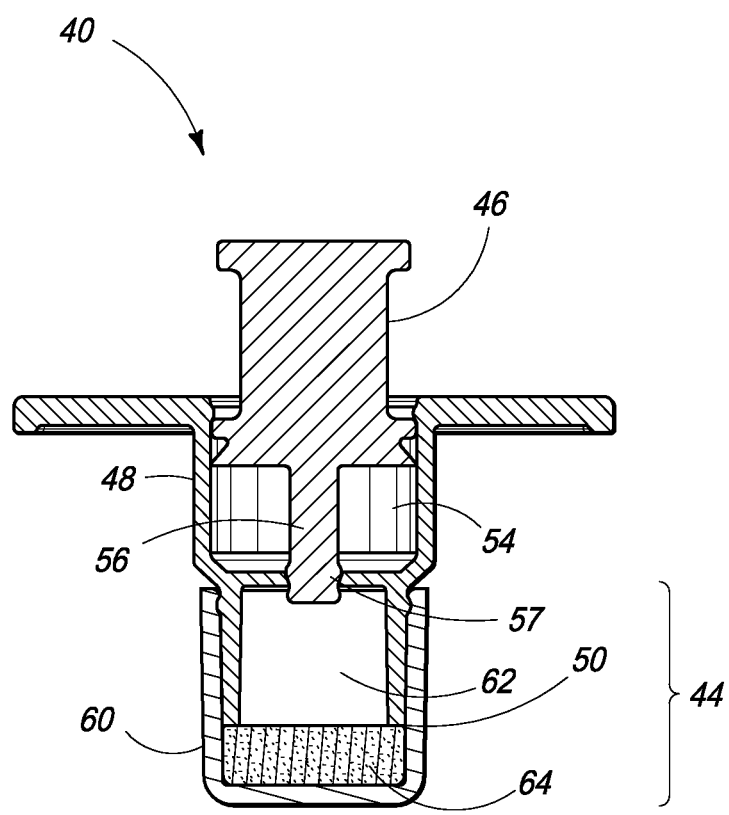
FIG. 9 is a diagrammatic cross-sectional view of the device shown in FIG. 6.

Referring next to FIG. 9, such shows a cross-sectional view of the embodied device 40 in an intact configuration. For utilization second component 44 can be removed and utilized to cleanse external surface of the port. Subsequently, first end 50 of the second component can be attached to the port and contents of the chamber 54 can be administered into the port by application of force to plunger 46. Alternatively, chamber 54 can be provided empty or can be provided to contain, for example, an anticoagulant agent and device 40 can be provided with plunger 46 in a forward position. Thus device 40 can be utilized for applications such as obtaining and/or testing of a blood sample from an individual by attaching first end 50 of the device to the port and repositioning of plunger 46 to draw fluid through the port into chamber 54.

Figure 10:
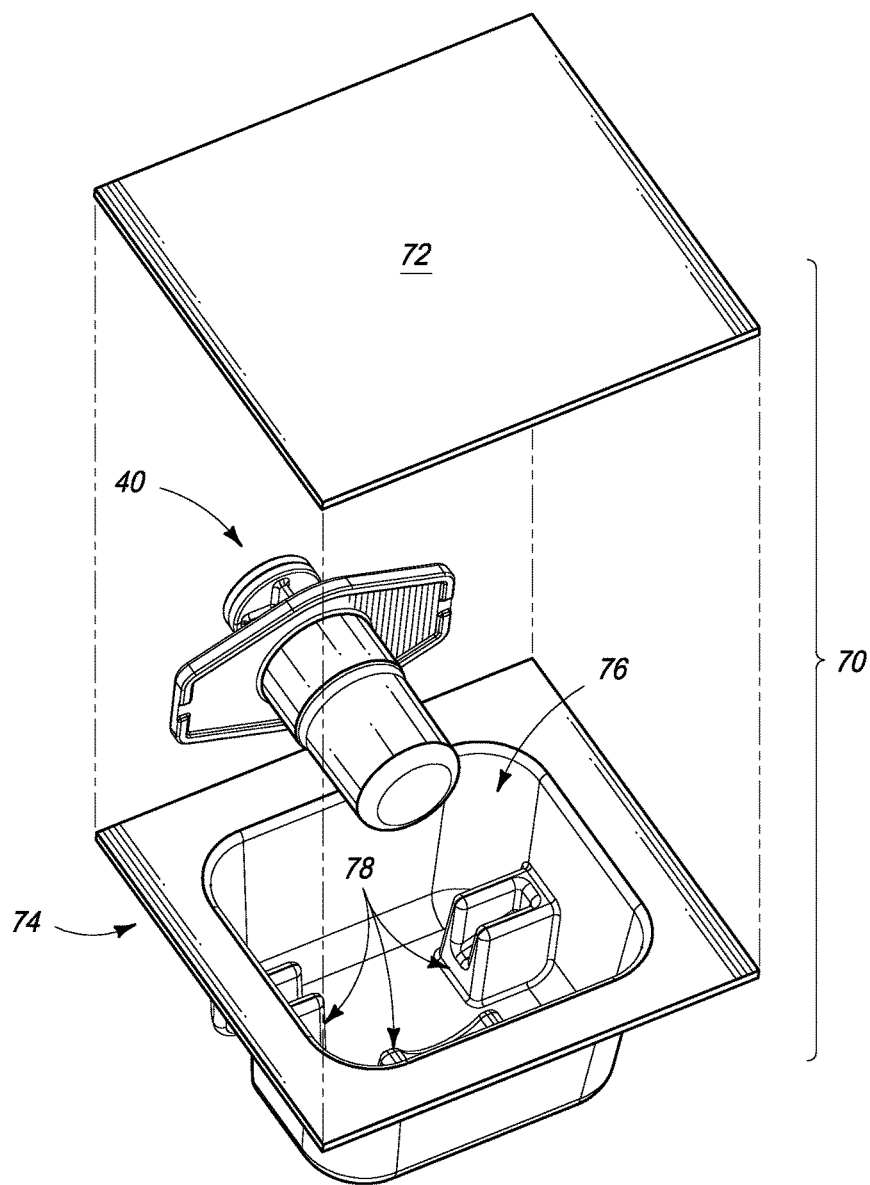
FIG. 10 is a diagrammatic view of an exemplary packaging concept for the device shown in FIG. 6.
Figure 11:
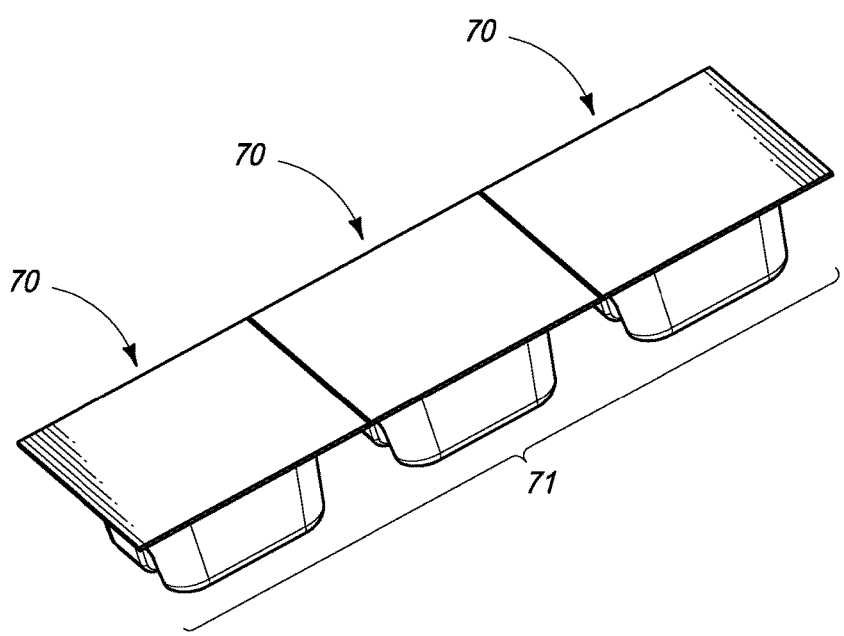
FIG. 11 shows a multi-pack packaging concept for the device shown in FIG. 6.

Referring to FIG. 10 packaging 70 for delivery, storage and/or disposal of the component for access device 40 is illustrated. Such packaging includes a lid 72 and a tray portion 74. Tray portion 74 has a cavity 76 with molded retainers 78 for positioning/retaining of the device and assisting in maintaining the integrity of the device and proper positioning of the plunger relative to the device chamber. Such packaging can be sealed and can be utilized to provide a sterile environment for device 40. As shown in FIG. 11 a series 71 of individual packaging unit 70 can be provided with individually sealed units to allow individual removal of units while maintaining sterility of additional units in the series.

Another alternative embodiment is described with reference to FIGS. 12-13. In this embodiment first component 42a is the same as the immediately preceding embodiment. However, referring to FIG. 12 second component 44a comprises a "dual cap" system. Cap housing 60a includes container portion 62 and a second cap extension 65 which houses a second container 66. Container 62 can contain an applicator material 64 such as the sponge-like materials described above. Similarly container 66 can also contain a sponge or other applicator material 67. Container 62 can further contain a cleansing agent such as those described above.

Container 66 can preferably contain one or more microbiocidal agents that differ in composition from the cleaning solution contained in the cleansing cap 62. An example agent composition within cap portion 65 can include from about 3% to about 11% $H_2O_2$. Additional components of the agent can include for example ethanol (from about 25% to about 60%) sodium citrate (from about 1% to about 4%), EDTA, peracetic acid (less than or equal to about 1%), and/or carbamide peroxide (less than or equal to about 11%). Preferably, the pH will be between about 5 and 10 and can be adjusted with NaOH or other appropriate base/acid to about pH 7.4 as needed based upon the physiological pH and biocidal activity. The presence of EDTA can provide sporocidal activity against for example bacillus spores by complexing Mn and can additionally help stabilize $H_2O_2$. Complexation or chelation of a variety of other metal ions with corresponding advantageous effects also is contemplated. In combination with $H_2O_2$ in the solution a synergistic and/or additive effect can be achieved. The disclosure does contemplate use of alternative chelators and pH stabilizers relative to those indicated.

It is to be noted that in some instances a similar solution having lower peroxide content may be included within the first container 62 and in particular instances may be present within the chamber of the first component.

Referring to FIG. 13 such shows an intact device prior to use. In port cleansing applications second component 44a is removed from the device and portion 60a is utilized to cover a port thereby contacting the port with the contents of container 62. Applicator material 64 can assist in applying the cleaning agent to external port surfaces. When the contents of chamber 54 are to be administered, component 44a is removed from the port and first component is attached to the port. Plunger 46 is depressed thereby injecting the contents of chamber 54 into the port. The syringe component is then removed from the port. A removable seal 68 can then be removed from second cap portion 65. Cap portion 65 can be placed over the port such that the contents of container 66 contact the port. Second component 44 can then be removed from the port or can be retained on the port until further port access or manipulation is desired. Additionally, a breakable joint (not shown) or an adhesive bond between the two sections of 44a can be formed so as to keep the two solutions separate but provide a ready means to disengage them from each other and utilize them for individual cleaning steps.

Figure 14:
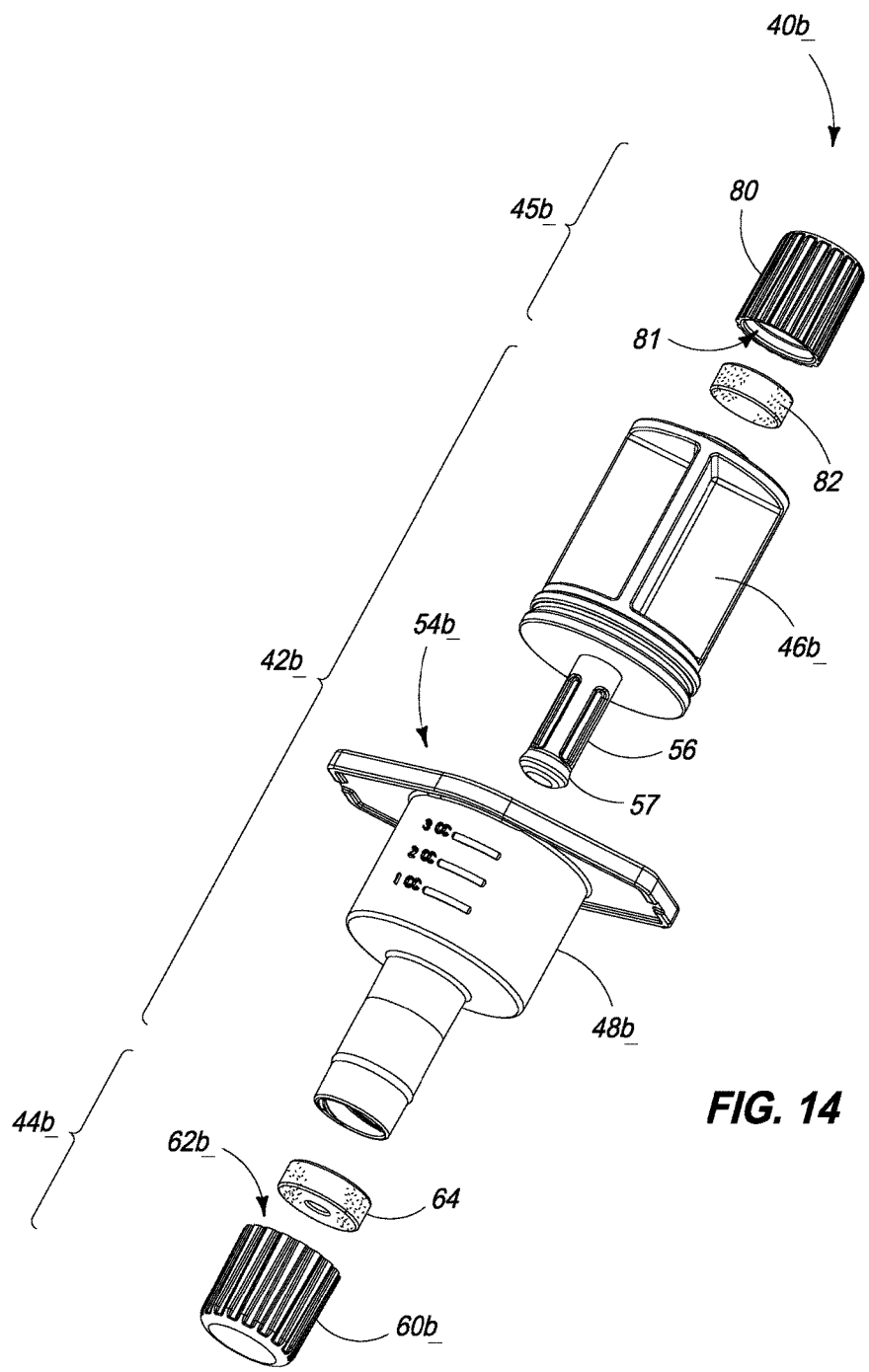
FIG. 14 is a diagrammatic exploded view of a device in accordance with another aspect of the disclosure.

Referring to FIG. 14 such shows an alternative embodiment wherein port access device 40b comprises a first component 42b, a second component 44b and a third component 45b where second component 44b and third component 45b are independently removable caps. As illustrated the caps are disposed initially at opposing ends of the device and are of differing size. However, alternative relative size and positioning of the caps on the device is contemplated. For example, first component 44b and second 45b can be disposed on top-side or bottom-side of wing extensions 51, 53 of chamber housing 48b.

For the example configuration illustrated, the larger cap (first component 44b) can be removed from the device and can be utilized for external port cleaning in a manner analogous to that described above. The second smaller cap (third component 45b) can be removed from the device after administration of the chamber contents and can be subsequently utilized as a port cap to protect the port until subsequent port access is desired as described above. Third component 45b optionally can contain an applicator material 82 and/or cleansing agent or microbiocidal agent as described above.

Alternative two-cap configurations include a device having a larger cap external to a smaller internal cap, the first cap being removable from the second cap where one of the first and second caps is configured for utilization as a port cap.

Figure 15:
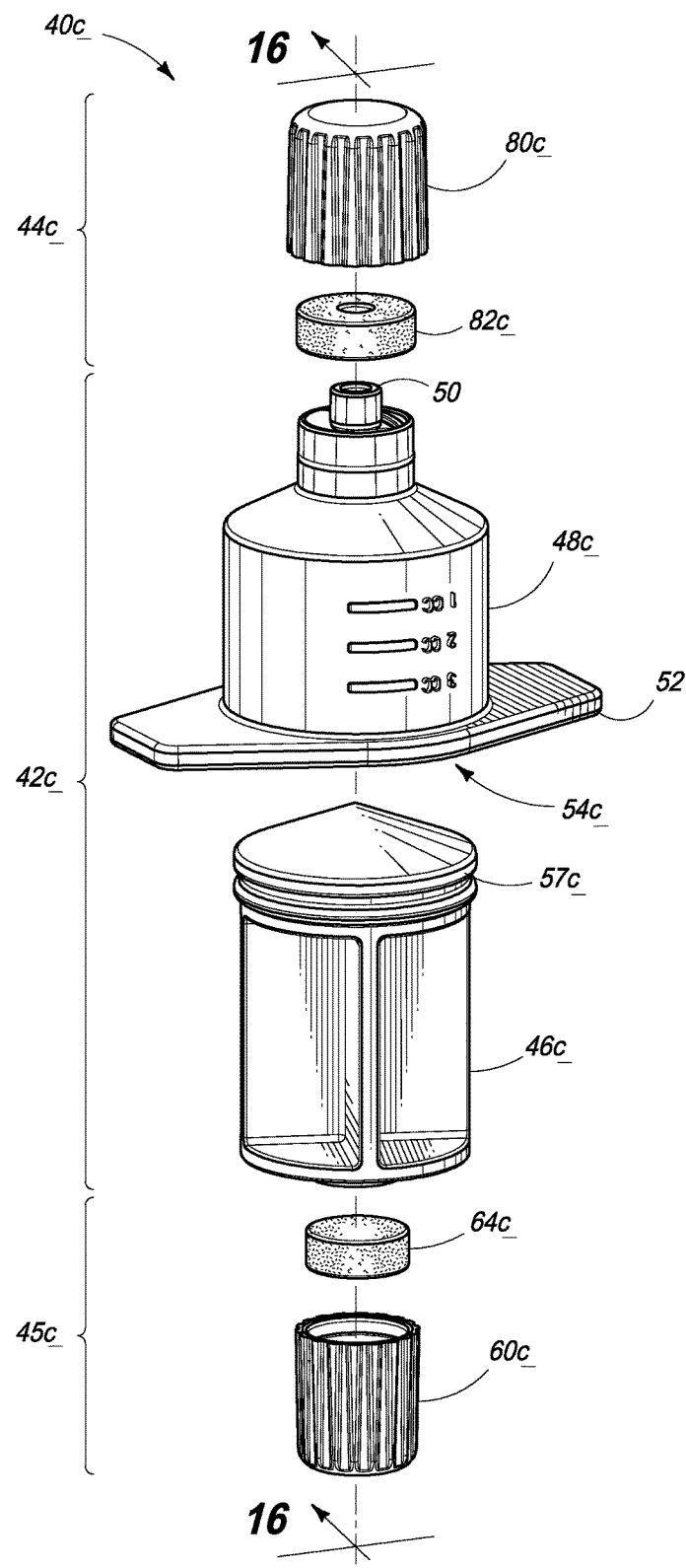
FIG. 15 is a diagrammatic exploded view of a device in accordance with another aspect of the disclosure.

In the device shown in FIG. 14, cap housing 60b of second component 44b and cap housing 80 of third component 45b can be of differing colors. As such, the caps can be color coded (or otherwise coded) to notify the user or other personnel of the status of the port or intravascular line. For example, a first color such as green can be utilized on all or a portion of cap housing 80 which will be retained on the port after use of the device to signify a properly sterilized port. It should also be noted that absorbent material 64, FIG. 14, and FIG. 15, 82c is illustrated with a central through-hole for more complete fitting and therefore more complete cleaning. Other such cleaning-enhancement shapes are contemplated. Cap housing 60b can be a second color (e.g., yellow or red) signifying the cleansing or other procedure being performed has not yet been completed. Accordingly, the caps can be utilized as an added safety measure to help ensure proper use and assist in maintaining sterility and appropriate record keeping. For example, the caps can allow visual monitoring and can be tracked by hospital pharmacy and/or central auditing software.

In addition to visual auditing of compliance to proper cleaning and maintenance of sterility, a barcode, radio frequency identification (RFID) and/or other pharmacy dispensary or inventory control system associated with the device can be utilized to provide an independent audit/compliance system.

Referring next to FIG. 15 such depicts an additional alternate embodiment which can utilize a conventional type syringe and plunger design and can utilize caps in accordance with the disclosure. Accordingly, first component 42c comprises a syringe housing 48c and can have a LEUR-LOK® fitting at first end 50. Plunger 46c can have a conventional type piston seal 57c configured to insert into second end 52 of housing 48c and form a seal with the walls of chamber 54c. Second component 44c can comprise a housing 60c which can for example have an internal receiving port which fits either internally relative to the LEUR-LOK® fitting or which fits over and covers the LEUR-LOK® fitting at first end 50 of first component housing 48c. Third component 45c can also have housing 80c configured such that it comprises an internal receiving port which fits either internally relative to a LEUR-LOK® fitting or which fits over and covers the LEUR-LOK® fitting (or which can have an alternative type fitting) based upon the type of port being cleansed.

Figure 16:
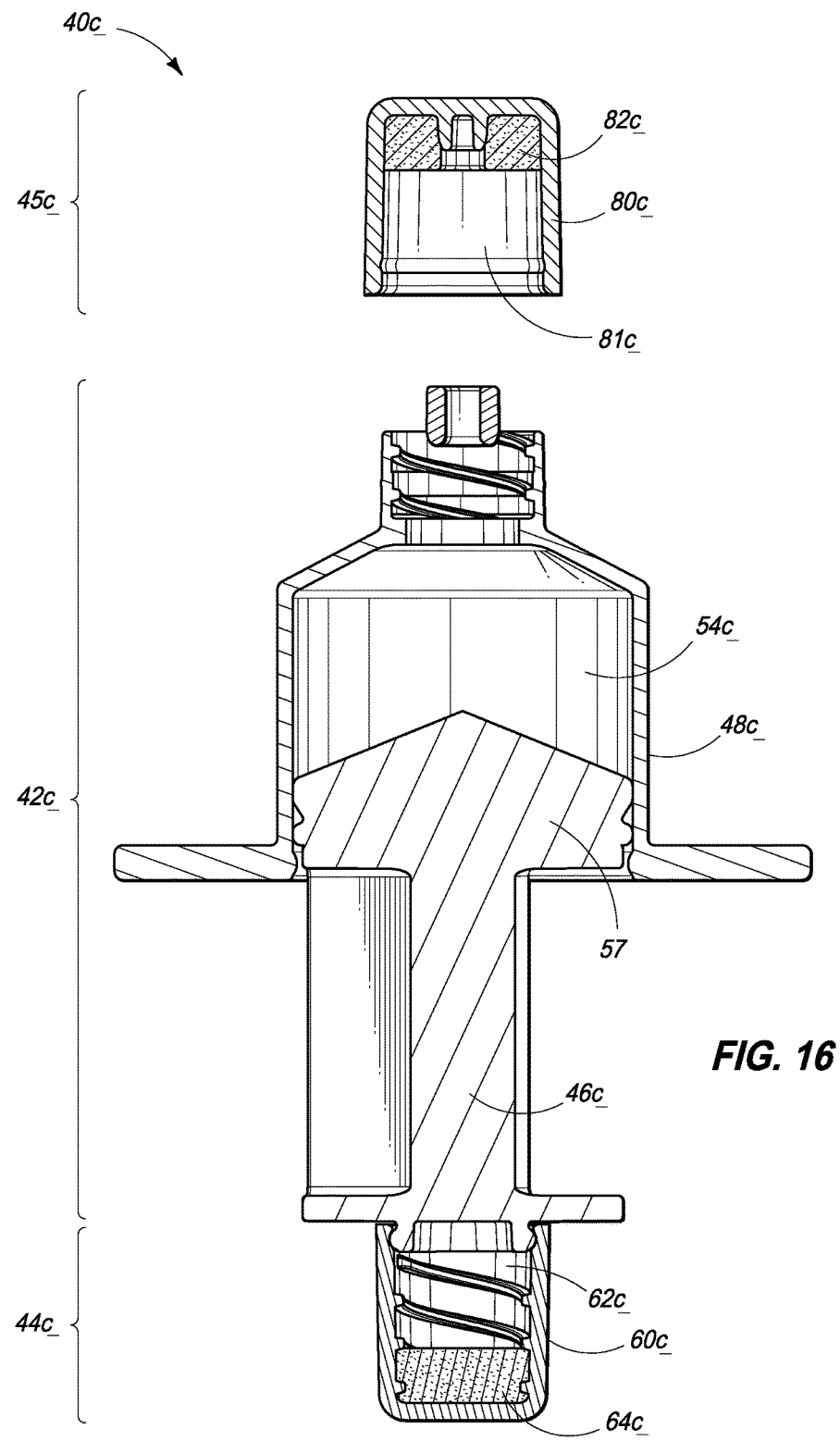
FIG. 16 is a diagrammatic cross-sectional side view of the device shown in FIG. 15.

A cross-sectional view of the device shown in FIG. 15 is illustrated in FIG. 16. Such shows the exemplary type of cap housings for covering LEUR-LOK®-type fittings. For example third component 45c has housing 80c comprising a portion of such housing which fits internally within a LEUR-LOK® type fitting thereby capping such fitting. In contrast second component 44c has housing 60c which is threaded to thread onto LEUR-LOK® type fitting. It is to be understood that the depiction is for illustrative purposes only and that either or both caps can have the threaded configuration or the snap in configuration. Cap housing 60c and 80c can further be color coded as described above.

The disclosure also contemplates dual cap system disposed at the distal (non-administration) end of the port cleaner device (not shown). In this dual cap system a first "green" cap can be reversibly joined to both the device and also back to front in a stack relationship relative to a second "yellow" cap. Each of the two caps can be, for example, a LEUR-LOK® type fitting cap, friction fit cap, etc. The green cap can contain the microbiocide composition described above. The yellow cap can contain for example the cleaning compositions discussed earlier or the microbiocide composition as contained in the green cap since in this configuration the yellow cap is not in contact with the administration end of the device.

Possible materials for caps include, but are not limited to, polyethylene, polypropylene, and/or copolymer materials. Further, the caps can preferably comprise a material or agent that is UV protective to preserve the integrity of hydrogen peroxide during storage, shipping, etc. Packaging may also contain UV protective materials to inhibit peroxide breakdown.

As mentioned above, devices of the disclosure can be utilized for withdrawing blood from an individual through an intravascular catheter or intravascular port. In particular applications, the device can be utilized directly for blood testing purposes. The device chamber can preferably have a chamber size in the range of 1 to 3 ml, with appropriate calibration marks as discussed above. Where whole blood is desired, depending upon the particular purpose for drawing, blood can be drawn into either a device having an empty chamber or into a device containing an anticoagulant such as EDTA, sodium citrate or alternative coagulant (such as discussed above). The device containing blood and anticoagulant can then be utilized directly in blood testing equipment or blood can be transferred to an alternative device for testing.

In applications where serum is desired, whole blood can be drawn into the device chamber and, after coagulation, the device containing the blood sample can be spun to separate the serum from the red blood cells. If anticoagulant is present in the device chamber, further separation can occur to isolate plasma. Alternatively, a filter such as a MILLI-PORE® (Millipore Corp., Bedford Mass.) filter can be fitted onto the device after a sample is drawn into the device chamber. Such technique can filter out red blood cells, white blood cells and platelets allowing serum to flow from the chamber while retaining the blood cells within the filter. Anticoagulants can optionally be provided within the chamber to allow transfer of blood cells or plasma if such is desired based upon the testing or other procedure to be performed (i.e., complete blood count, CBC, platelet count, reticulocyte count, T and B lymphocyte assays and chemistries).

An appropriate filter can also be utilized to filter out particulates during drawing of a blood sample from an individual into the chamber.

Figure 17:
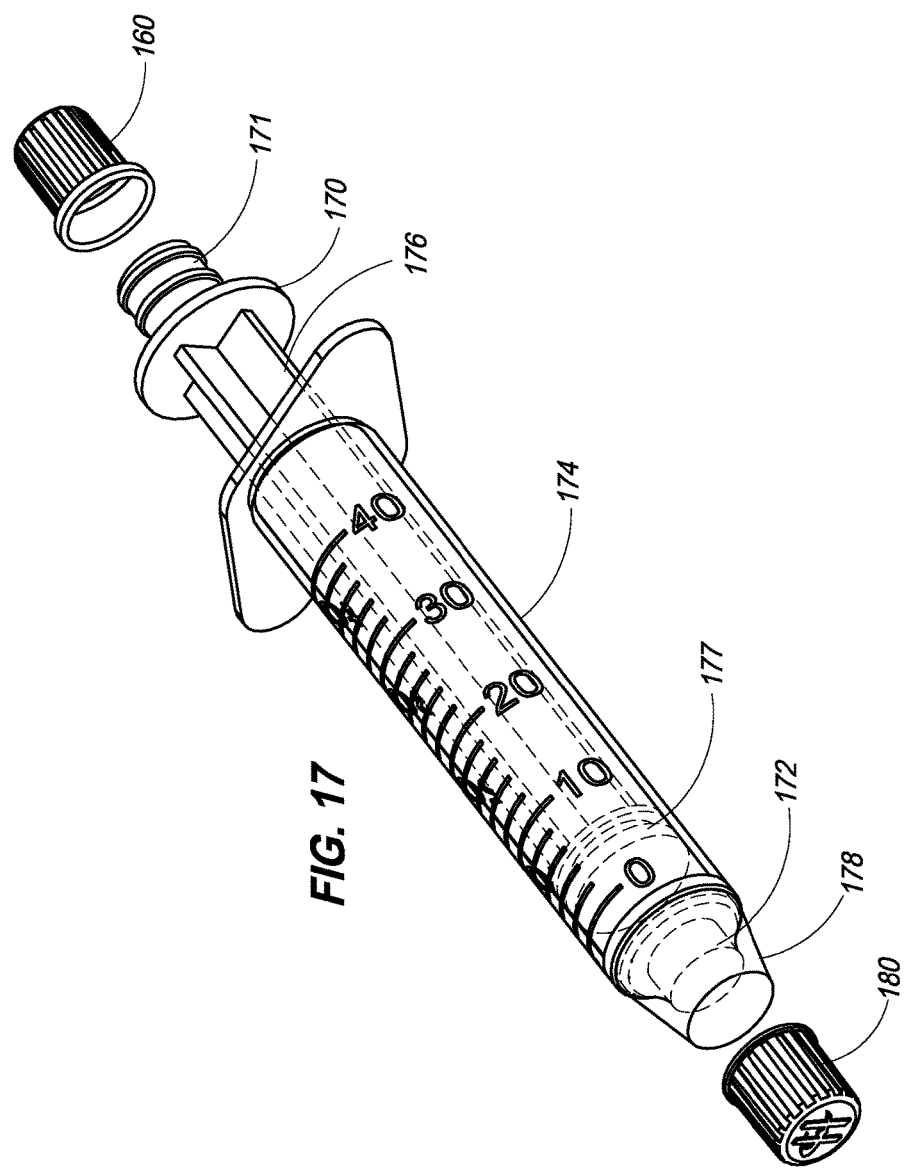
FIG. 17 is a diagrammatic view of a device in accordance with another aspect of the disclosure.
Figure 18:
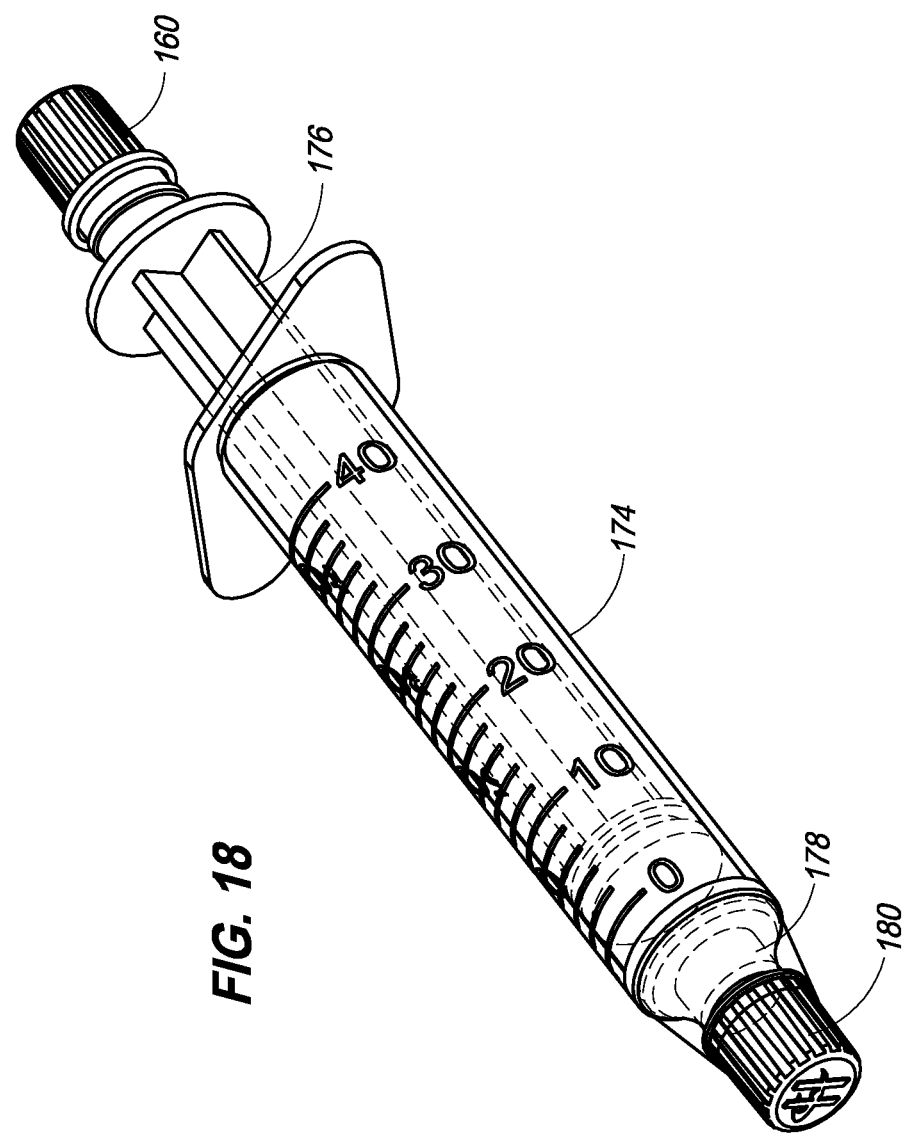
FIG. 18 is a diagrammatic view of a device in accordance with another aspect of the disclosure.
Figure 19:
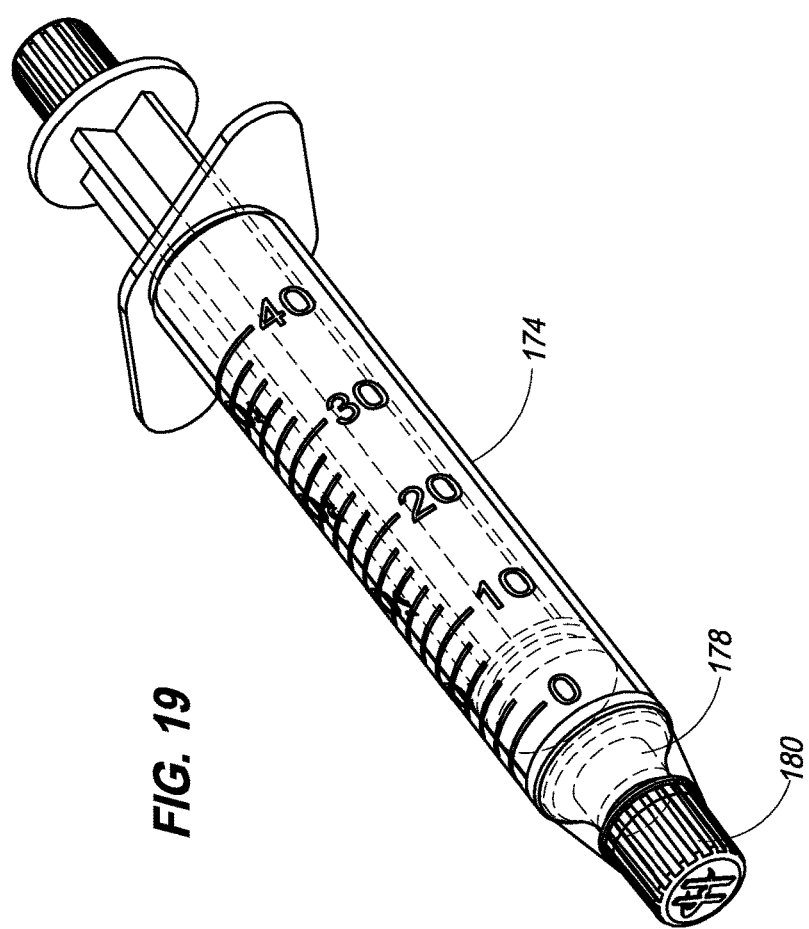
FIG. 19 is a diagrammatic view of a device in accordance with another aspect of the disclosure.

Referring to FIGS. 17-19 an alternative embodiment is shown that may be utilized during or for administration purposes. In accordance with example implementations, this assembly may be utilized to provide solutions via an access port such as a LEUR-LOK® port.

Accordingly, syringe cylinder 174 and can have a LEUR-LOK® fitting at first end 172. Plunger 176 can extend from a conventional type piston seal 177 configured to insert into the second end of cylinder 174 and form a seal with the walls thereof, to another end 170. Accordingly, cylinder 174 can extend from an opening configured to receive plunger 176 to first end 172, with end 172 configured to couple with a needle and/or medical tubing. Cap 180 can comprise a housing which can for example have an internal receiving port which fits either internally relative to the LEUR-LOK® fitting or which fits over and covers the LEUR-LOK® fitting at first end 172. Cap 160 can be configured such that it comprises an internal receiving port which fits either internally relative to a LEUR-LOK® fitting or which fits over and covers the LEUR-LOK® fitting (or which can have an alternative type fitting) based upon the type of port being cleansed. In some embodiments, appendage 171 can be part of or extend from end 170 and be configured as a male LEUR-LOK® fitting and cap 160 is configured to couple therewith. Accordingly, the caps of the disclosure can be configured to couple to the assembly, such as, for example, end 172 and/or appendage 171. Caps 180 and 160 can be colored as described above with the green cap being 160 and the yellow cap being 180.

Referring to FIGS. 18 and 19, the assembly of FIG. 17 is shown in alternative configurations. For example, the assembly of FIG. 17 can include barrier material 178 extending from a portion of cylinder to end 172. This barrier material may seal the contents of cylinder 174 when not in use for example. Referring to FIGS. 18 and 19 barrier material 178 may extend to encompass at least a portion of cap 180. This barrier material can include but is not limited to translucent fracturable material such as thin polymeric sheet material, for example.

With reference to FIGS. 20-28 the disclosure also contemplates dual cap system disposed at the distal end of an administration device. In this dual cap system a first "green" cap 160 can be reversibly joined to both the device and also back to front in a stack relationship relative to a second "yellow" cap 180. Each of the two caps can be, for example, a LEUR-LOK® type fitting cap, friction fit cap, etc. The green cap can contain the microbiocide composition described above. The yellow cap can contain for example the cleaning compositions discussed earlier or the microbiocide composition as contained in the green cap since in this configuration the yellow cap is not in contact with the administration end of the device.

Figure 20:
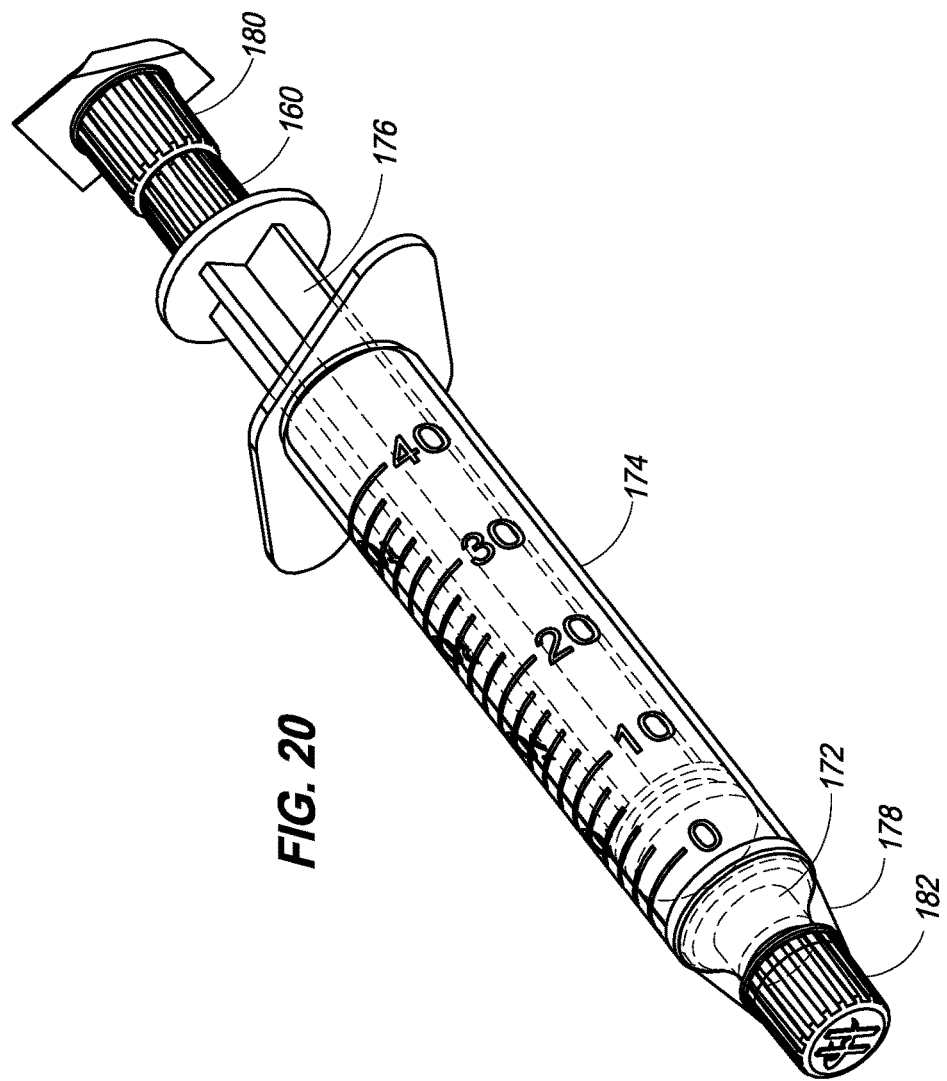
FIG. 20 is a diagrammatic view of a device in accordance with another aspect of the disclosure.
Figure 21:
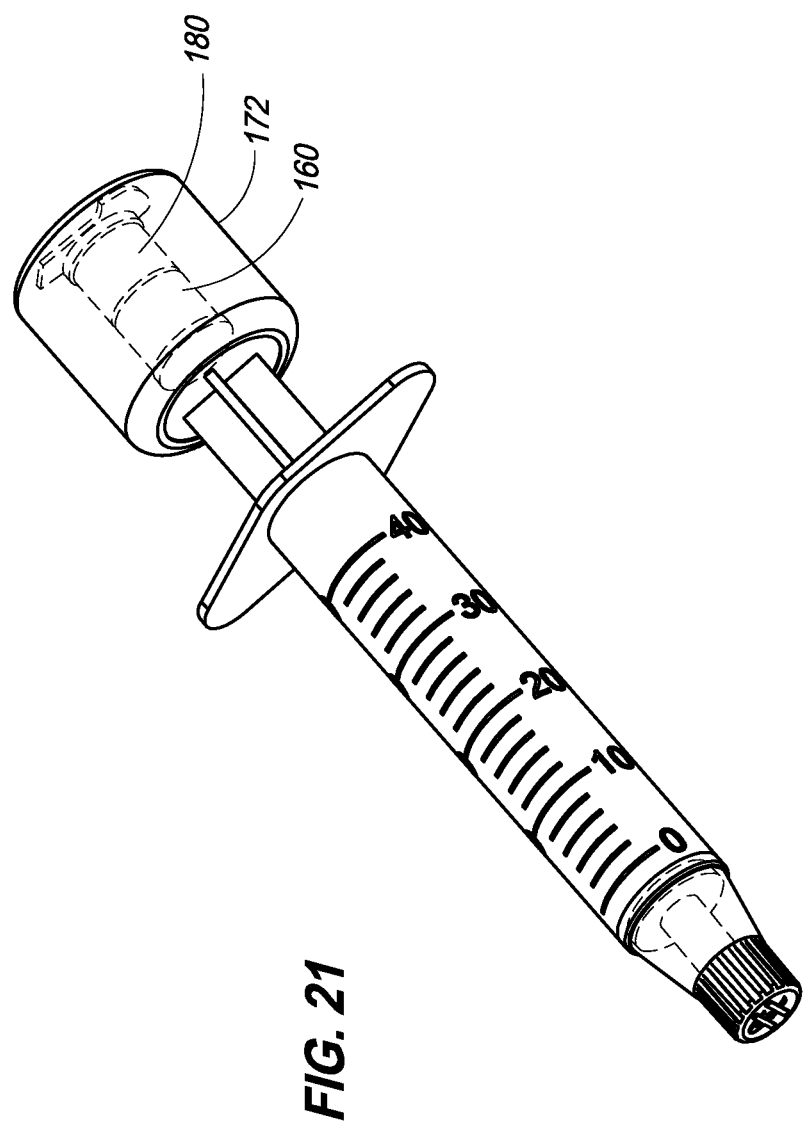
FIG. 21 is a diagrammatic view of a device in accordance with another aspect of the disclosure.

In an alternative embodiment as shown in FIGS. 20 and 21, for example, caps 180 and 160 can be removably coupled back-to-back with the cap 180 releasably sealed and the cap 160 coupled to plunger 176. Referring to FIG. 21, sealing both caps in a barrier material 184 is also contemplated. With reference to both these Figs, an additional cap 182 may be provided that may or may not include an applicator and/or solution.

Figure 22:
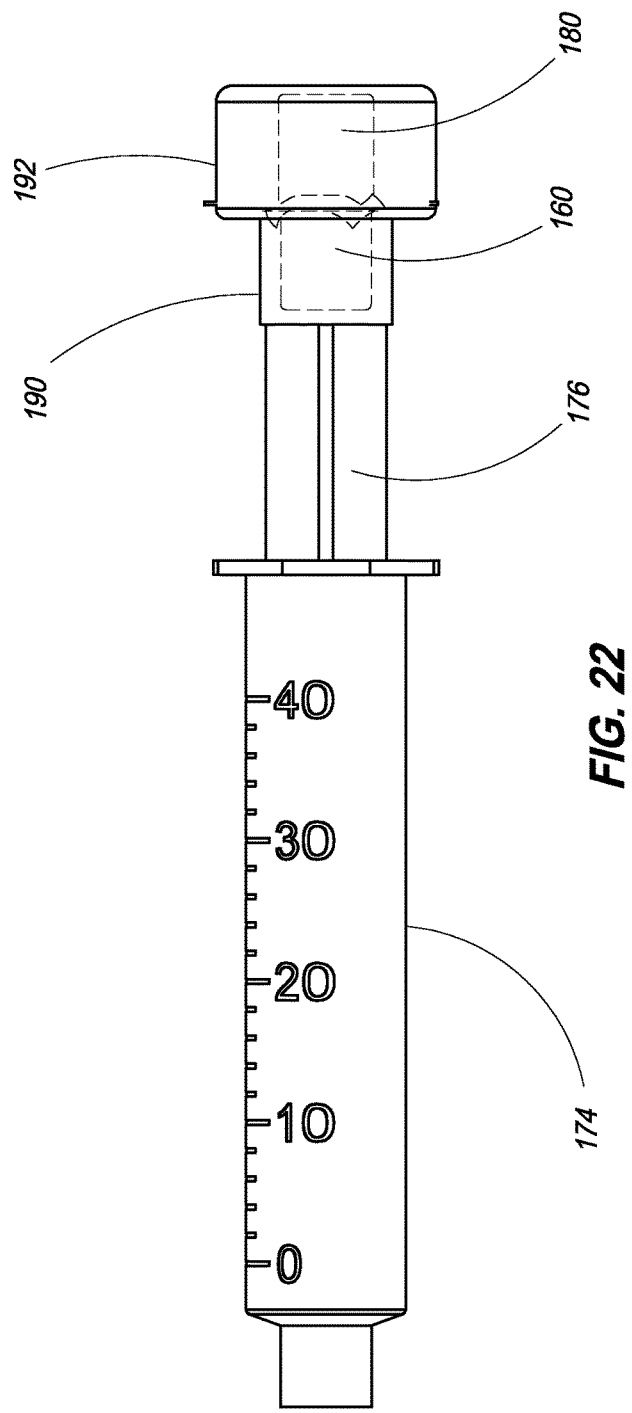
FIG. 22 is a diagrammatic view of a device in accordance with another aspect of the disclosure.
Figure 23:
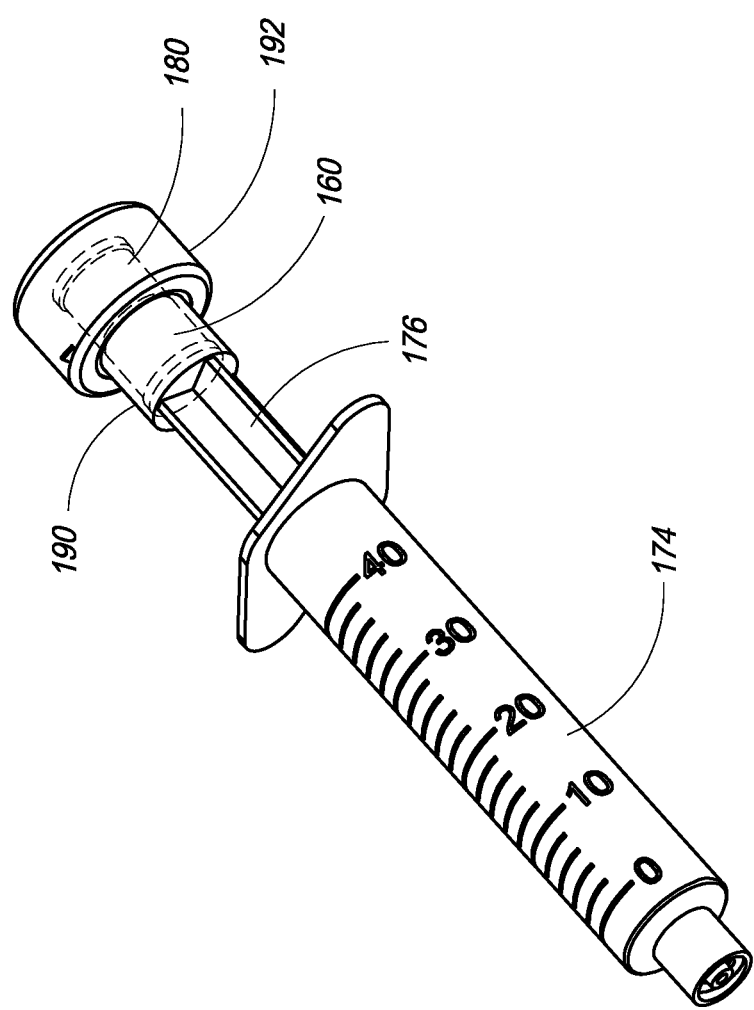
FIG. 23 is a diagrammatic view of a device in accordance with another aspect of the disclosure.
Figure 24:
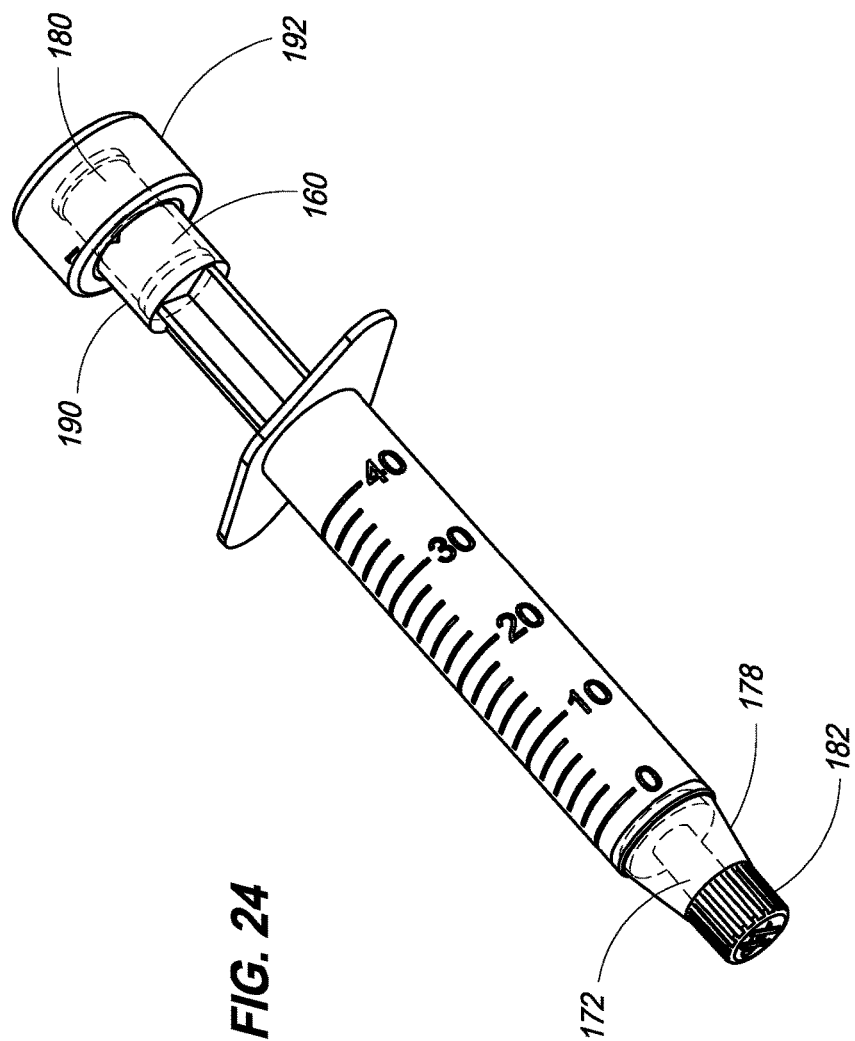
FIG. 24 is a diagrammatic view of a device in accordance with another aspect of the disclosure.
Figure 25:
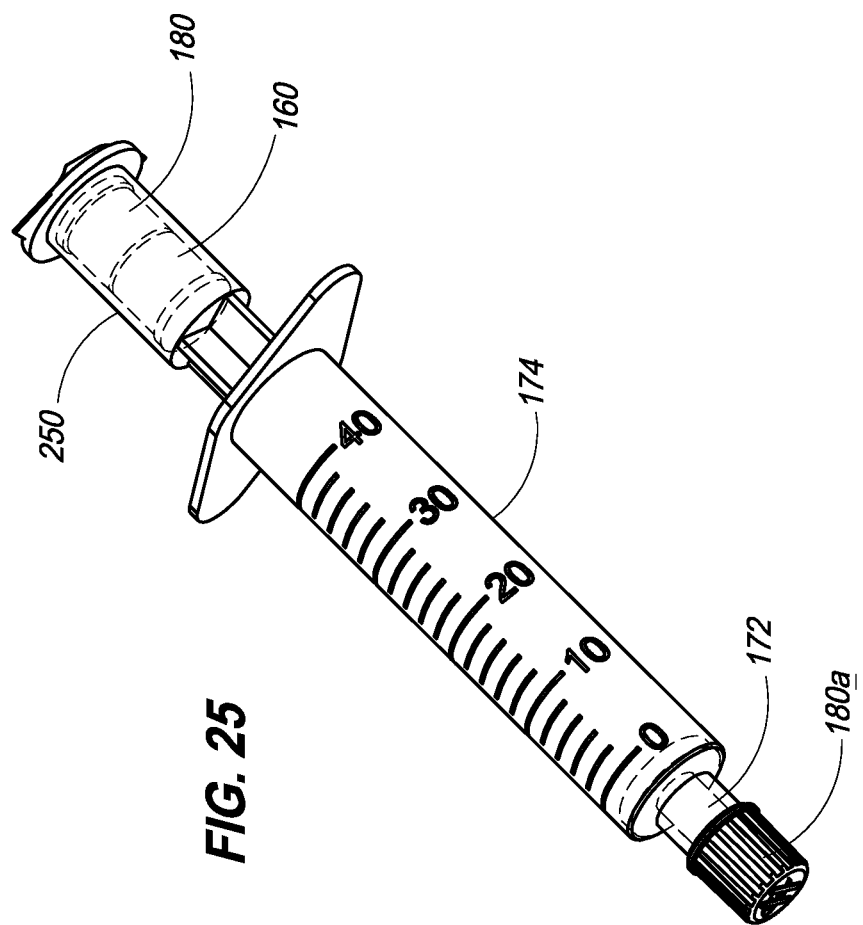
FIG. 25 is a diagrammatic view of a device in accordance with another aspect of the disclosure.
Figure 26:
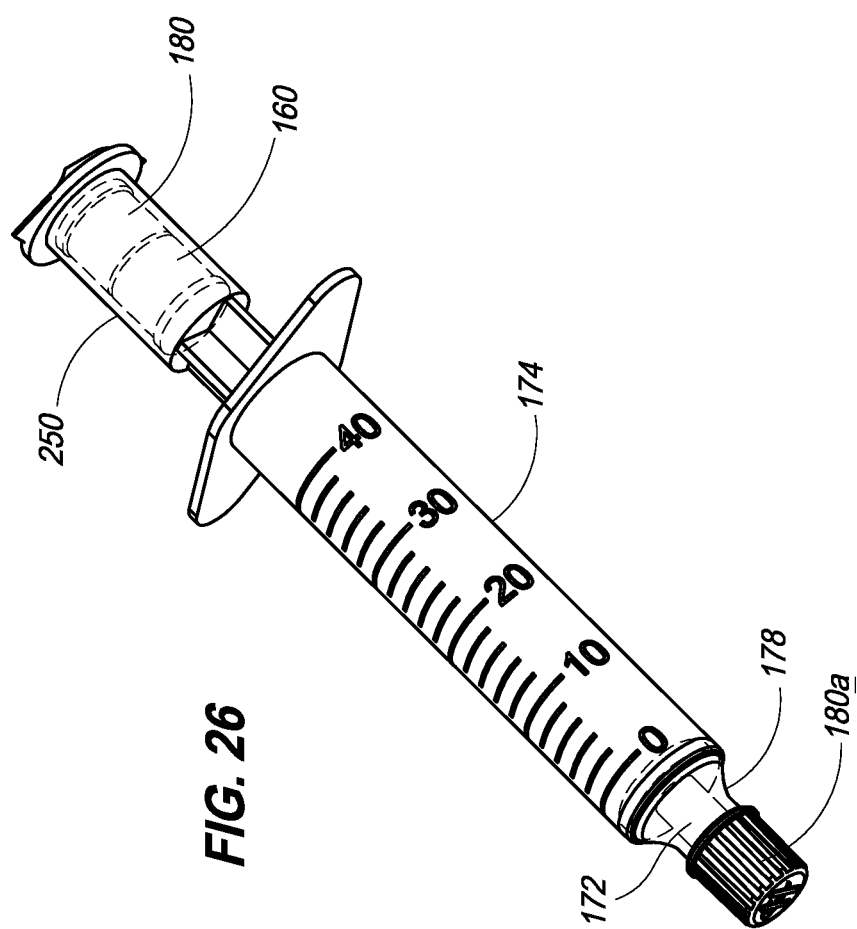
FIG. 26 is a diagrammatic view of a device in accordance with another aspect of the disclosure.
Figure 27:
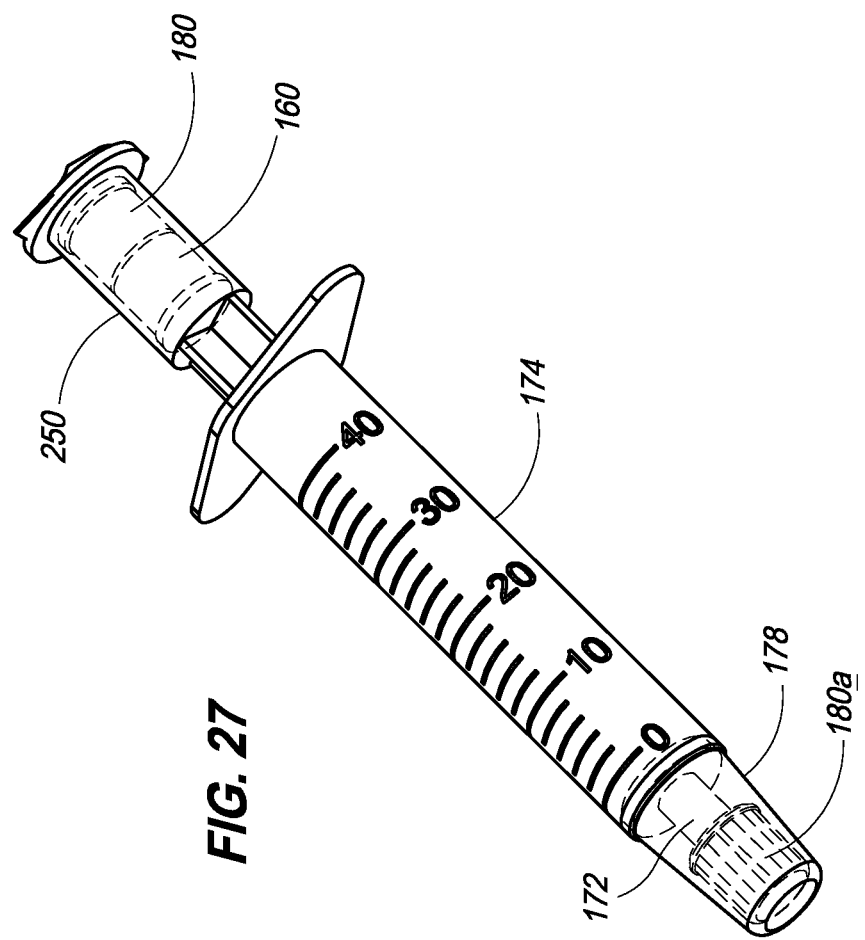
FIG. 27 is a diagrammatic view of a device in accordance with another aspect of the disclosure.

Referring to FIGS. 22 and 23, in accordance with another embodiment, caps 160 and 180 may be aligned front-to-front for example with both caps either sharing a releasable seal or having individual releasable seals, for example. Piston 176 can be configured with a housing 190 that is configured to contain one, both or a portion of either of caps 160 and/or 180. Further, a barrier material 192 may be provided to enclose any portion of either of both of caps 160 and 180. In the shown embodiment, cap 160 resides almost entirely within housing 190 while cap 180 resides within barrier material 180. In the instant embodiment barrier material 192 may be configured as a rigid cover that is releasably attached to piston 176, for example. Yet another view of this embodiment is shown in FIG. 24 depicting the device including the blue cap 182 as well as barrier material 178 encompassing both end 172 and blue cap 182, for example.

In accordance with another embodiment of the disclosure a syringe is shown having a plunger with housing 250. Housing 250 can be configured to receive and/or house at least two caps, such as caps 180 and 160 shown. In accordance with example implementations, these caps can be yellow and green caps respectively. These caps can be configured within housing 250 in a front-to-back configuration as shown with the releasable seals being independent of other caps. One or more of these caps can be placed in housing 250 in the proximal end of the plunger shaft, then the housing sealed to form a cavity at the base of the plunger or over a side access entry to the cap chamber. The housing may be sealed with a cover that may be attached to the plunger via a hinge, for example. The cover may also be releasably attached as a polymeric foil seal or snap-fit, for example.

Figure 28:
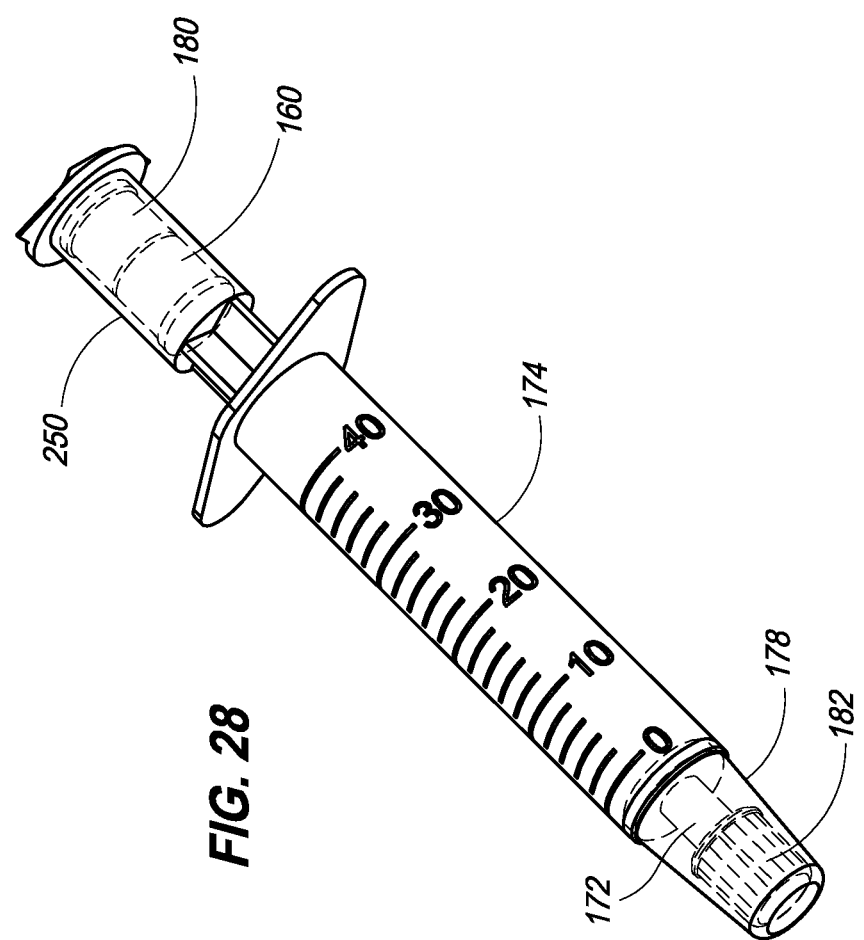
FIG. 28 is a diagrammatic view of a device in accordance with another aspect of the disclosure.

Referring to FIGS. 25-28, an additional cap such as a yellow cap 180a may be provided with the device. In accordance with different implementations, barrier material 178 may be provided to encompass all of end 172 and cap 180a, or at least a portion of cap 180a. Referring to FIG. 28, the device can be configured with a blue cap 182, for example. Cap 182 which can include a sponge and cleaning/disinfection fluid, could be placed on the tip of the syringe. Barrier material such as polymeric barrier could cover both the cap and the distal syringe portion or whole syringe to prevent particulate and microbial contamination and to maintain a sterile environment after terminal sterilization. In accordance with other implementations, end 172 may be configured to have barrier material such as a polymeric/metallic foil seal over end 172 to prevent mixing with the fluid in the cap, which could be used to protect male luer or slip fit connectors from IV lines or syringes.

It is to be understood that any of the devices above can be utilized for cleansing purposes, for administration purposes or for blood drawing/testing purposes. Methodology will be analogous with variation based upon the particular device utilized as described above.

Figure 29:
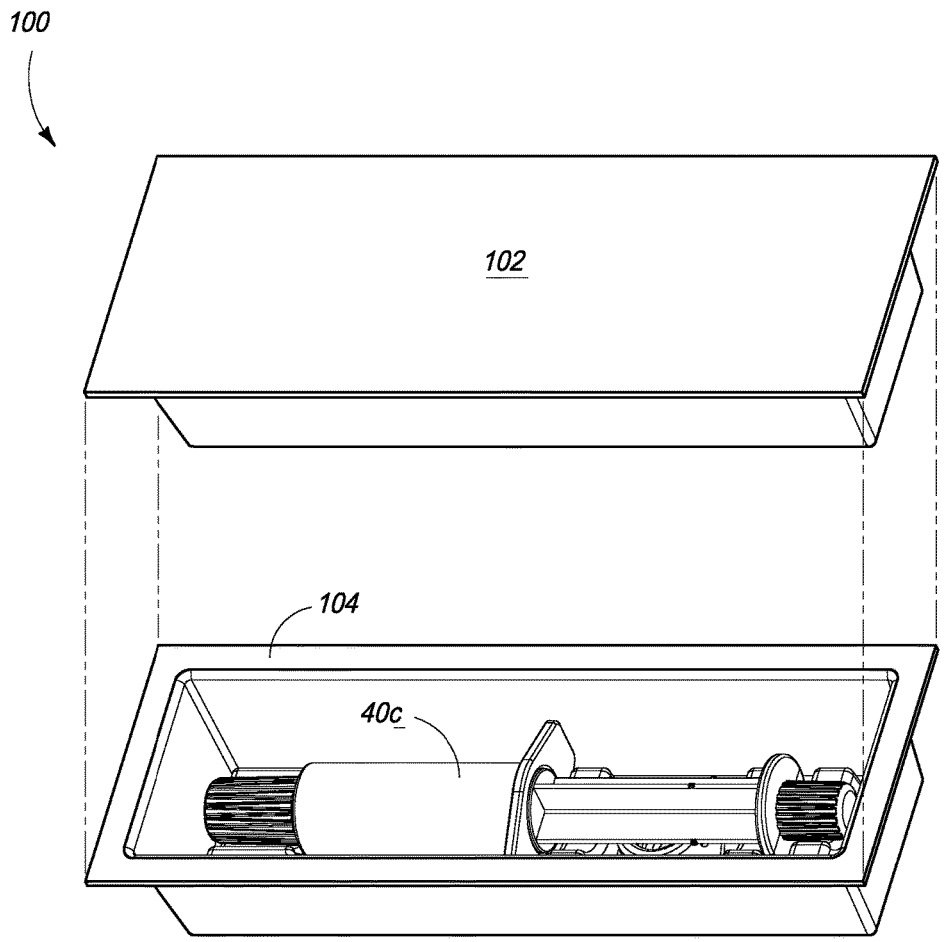
FIG. 29 is a diagrammatic isometric view of a packaging concept in accordance with one aspect of the disclosure.
Figure 30:
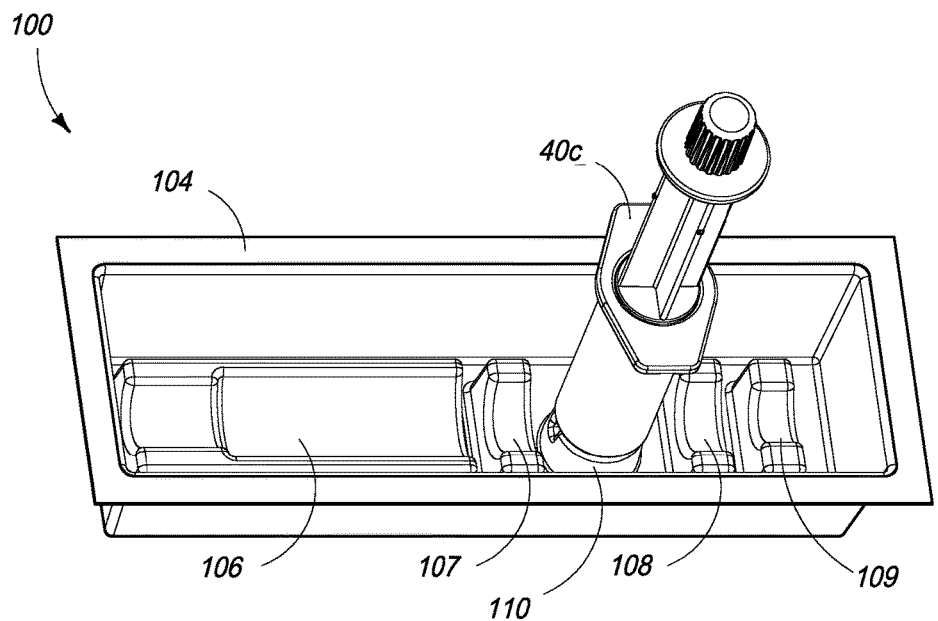
FIG. 30 is a diagrammatic isometric view of the packaging concept shown in FIG. 29.
Figure 31:
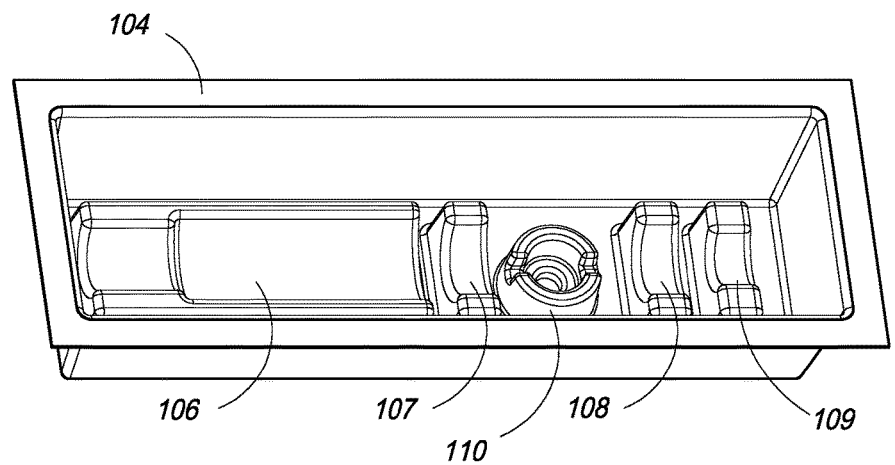
FIG. 31 is another diagrammatic isometric view of the packaging concept shown in FIG. 29.

Example device packaging is illustrated in FIGS. 29-31. Packaging 100 can include a lid portion 102 and a packaging tray 104 as shown in FIG. 29. Referring to FIGS. 30 and 31 packaging tray 104 can be a molded tray which has integrally molded retaining features which conform to the shape of a device 40c in accordance with the disclosure. Preferably the molded features conform to the shape of the device in the non-deployed position for shipment, storage, etc. Accordingly tray 104 can have one or more integrally molded retainer features 106, 107, 108 and 109. Tray 104 can also comprise an integrally molded receiving stand 110 which can be configured to receive device 40c in an upright position as depicted in FIG. 30. Such receiving stand can allow device 40c to be inserted and retained during administrative procedures or after use. Tray 104 may also be used for device disposal purposes.

Figure 32:
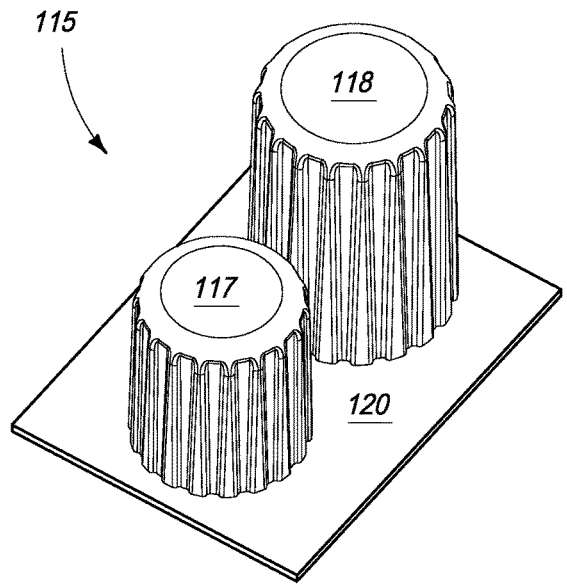
FIG. 32 is a diagrammatic isometric view of a set of components in accordance with one aspect of the disclosure.
Figure 33:
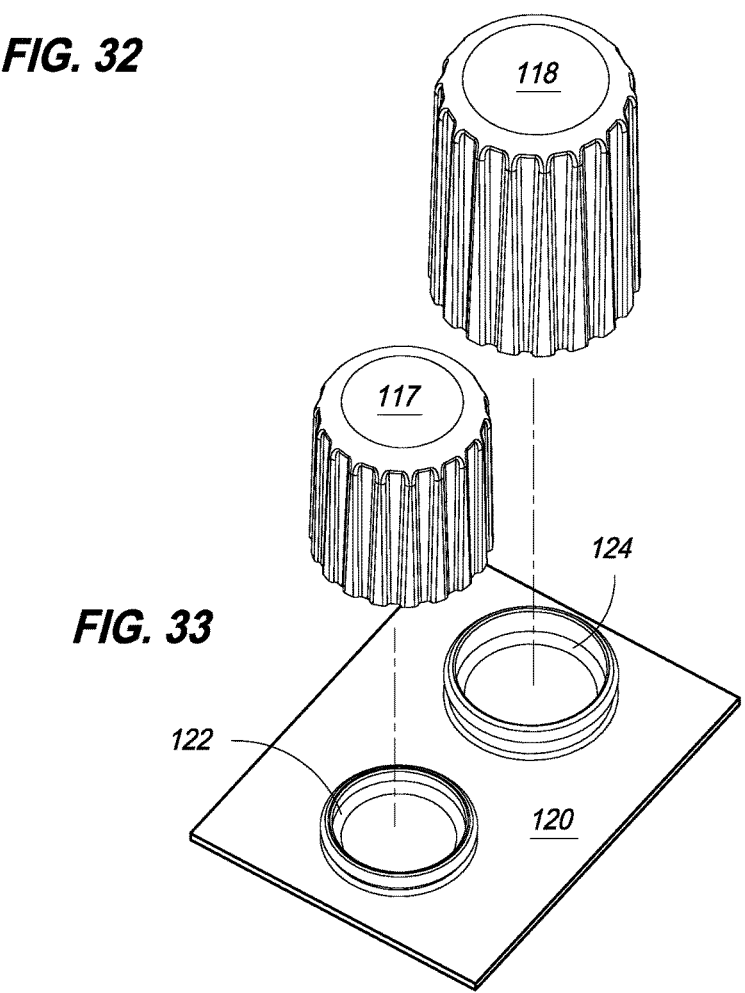
FIG. 33 is an exploded view of the set of components depicted in FIG. 32.

Device caps in accordance with the disclosure can be utilized independent of the devices for cleansing and protection of alternative access catheters and ports such as intravascular, peritoneal dialysis, urinary ports and catheters, etc. Accordingly, the caps can be packaged independently in pairs (one each of two differing sizes, colors, etc., in groups or in bulk, of one or more colors). FIGS. 32-33 show an example two cap packaging system 115 having a first cap 117 which can be for example a yellow cap and which can preferably be a LEUR-LOK® type cap and a second cap 118 which can be, for example, a green cap and which can also be a LEUR-LOK®. Packaging system 115 can comprise a packaging tray 120 and as illustrated in FIG. 33 can include integrally molded appropriate receiving ports/receiving rings 122, 124. Where additional or fewer caps are to be packaged together tray 120 can have an appropriate number of receiving ports for receiving and reversibly retaining the caps. Where the caps differ in size (diametric), the ports can also be of differing size as appropriate. It is to be understood that the caps may be provided in groups such as one green and four yellow caps per package or any other appropriate number depending upon the particular procedure for which they will be utilized with the number and size of package ports corresponding to the number and size of various caps.

Figure 34:
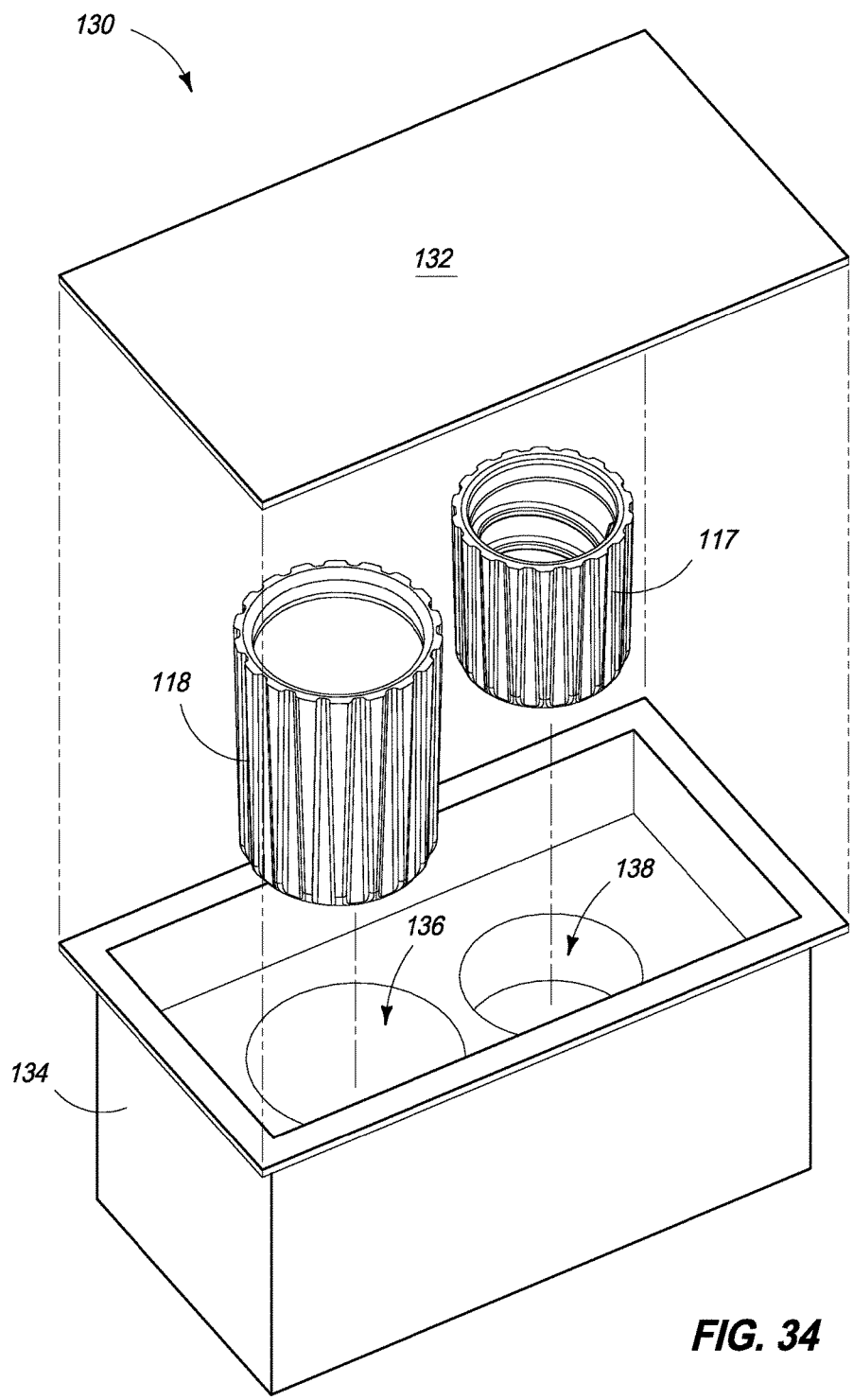
FIG. 34 is a diagrammatic exploded view of a packaging concept in accordance with one aspect of the disclosure.

Referring next to FIG. 34 an alternative packaging system 130 is illustrated. Packaging system 130 comprises a lid 132 and a tray 130 having integral receiving ports 136 and 138 for receiving caps 117 and 118. As discussed above alternative numbers and sizes of receiving ports can be provided based upon the number and sizes of caps to be utilized.

Where caps are provided in bulk, such may be individually packaged and may be provided individually in sheets or on strips. Caps can alternatively be provided with catheter or line/import devices. Such can be included in common packaging either loose or attached to a port catheter or line to be used for port cleaning and/or protection after package opening and/or while the device is in use. In some instances the cap(s) can be packaged in one or more sub-packages included within a larger package enclosing the catheter device.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect.

The invention claimed is:

1. A syringe assembly comprising:
a syringe cylinder extending from an opening configured to receive a plunger to an end configured to couple with a needle and/or medical tubing;
a plunger extending from one end to a sealed end;
at least one port cap configured to couple to the one end and another port cap configured to couple with the one port cap, the one and another port caps abutting each other when coupled, and wherein each of the port caps is configured to releasably couple to a line port and comprises:
a structure extending from a surface of the caps, the structure being complimentary to another structure of the line port; and
one or both of a sponge-type applicator material and a cleansing solution; and
a barrier material encompassing both the one cap and the other cap.

2. The syringe assembly of claim 1 wherein the one port cap further comprises both a sponge-type applicator material and a cleansing solution.

3. The syringe assembly of claim 1 wherein both port caps and the one end are configured to couple via a LEUR-LOK fitting.

4. The syringe assembly of claim 1 wherein the one end defines an internal fitting and the one port cap is configured to couple with the one end outside the internal fitting.

5. The syringe assembly of claim 1 wherein both port caps are configured to couple with the same size port.

6. The syringe assembly of claim 1 wherein the barrier material encloses the sponge-type applicator material and/or cleansing solution within the other port cap.

7. The syringe assembly of claim 1 wherein both port caps are the same size.

8. The syringe assembly of claim 1 wherein the structure of each of both port caps comprises internal threading.

* * * * *

UNITED STATES PATENT AND TRADEMARK OFFICE
CERTIFICATE OF CORRECTION

PATENT NO. : 9,592,375 B2
APPLICATION NO. : 13/781196
DATED : March 14, 2017
INVENTOR(S) : Patrick O. Tennican It is certified that error appears in the above-identified patent and that said Letters Patent is hereby corrected as shown below:

Column 10, Line 54 – Replace "cylinder 174 and can have" with --cylinder 174 can have--

Column 11, Line 14 – Replace "of cylinder to end 172" with --of cylinder 174 to end 172--

Column 11, Line 49 – Replace "of either of both of caps 160" with --of either or both of caps 160--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*